(12) United States Patent
Tanimori et al.

(10) Patent No.: US 10,989,676 B2
(45) Date of Patent: Apr. 27, 2021

(54) GAMMA-RAY IMAGE ACQUISITION DEVICE AND GAMMA-RAY IMAGE ACQUISITION METHOD

(71) Applicant: KYOTO UNIVERSITY, Kyoto (JP)

(72) Inventors: Toru Tanimori, Kyoto (JP); Atsushi Takada, Kyoto (JP); Tetsuya Mizumoto, Kyoto (JP); Dai Tomono, Kyoto (JP)

(73) Assignee: KYOTO UNIVERSITY

( * ) Notice: Subject to any disclaimer, the term of this patent is extended or adjusted under 35 U.S.C. 154(b) by 249 days.

(21) Appl. No.: 16/305,161

(22) PCT Filed: May 29, 2017

(86) PCT No.: PCT/JP2017/019936
§ 371 (c)(1),
(2) Date: Mar. 1, 2019

(87) PCT Pub. No.: WO2017/209059
PCT Pub. Date: Dec. 7, 2017

(65) Prior Publication Data
US 2020/0319123 A1    Oct. 8, 2020

(30) Foreign Application Priority Data

May 30, 2016    (JP) .............................. JP2016-107780

(51) Int. Cl.
*G01N 23/20066*    (2018.01)
*G01T 1/161*    (2006.01)
(Continued)

(52) U.S. Cl.
CPC ....... *G01N 23/20066* (2013.01); *G01T 1/161* (2013.01); *G01T 1/172* (2013.01);
(Continued)

(58) Field of Classification Search
CPC ........... G01N 23/20066; G01N 33/383; G01N 2223/646; G01N 33/20; G01T 1/2935;
(Continued)

(56) References Cited

U.S. PATENT DOCUMENTS

| 5,821,541 A | 10/1998 | Tümer | 250/370.09 |
| 2013/0248719 A1* | 9/2013 | Volokh | A61B 6/03 250/362 |

(Continued)

FOREIGN PATENT DOCUMENTS

| JP | 2000-019254 A | 1/2000 |
| JP | 2013-200306 A | 10/2013 |

(Continued)

OTHER PUBLICATIONS

Shinichiro Takeda, et al., "Applications and imaging techniques of a Si/CdTe Compton gamma-ray camera", Physics Procedia, 2012, vol. 37, pp. 859-866.

(Continued)

*Primary Examiner* — David P Porta
*Assistant Examiner* — Meenakshi S Sahu
(74) *Attorney, Agent, or Firm* — Ostrolenk Faber LLP

(57) ABSTRACT

A gamma-ray image acquisition device (1) acquires the direction and energy of a target scattered gamma-ray generated by Compton scattering of an incident gamma-ray and acquires the direction and energy of a recoil electron. These pieces of information are used to acquire the incident direction and energy of the incident gamma-ray. The gamma-ray image acquisition device (1) acquires a two-dimensional image by imaging spectroscopy based on the incident directions and energies of a plurality of incident gamma-rays, the two-dimensional image being an image in which each pixel corresponding to each incident direction includes energy distribution information. In the two-dimen- (Continued)

sional image, the area and the solid angle of an imaging range are proportional to each other. This enables acquiring the distribution of gamma-ray intensities without depending on distance and thereby acquiring an image that indicates more useful information than conventional images.

13 Claims, 18 Drawing Sheets

(51) Int. Cl.
```
G01T 1/172      (2006.01)
G01T 1/29       (2006.01)
G01T 7/00       (2006.01)
A61B 6/03       (2006.01)
G01N 33/20      (2019.01)
G01N 33/38      (2006.01)
```
(52) U.S. Cl.
CPC .............. *G01T 1/2935* (2013.01); *G01T 7/00* (2013.01); *A61B 6/037* (2013.01); *G01N 33/20* (2013.01); *G01N 33/383* (2013.01); *G01N 2223/646* (2013.01)

(58) Field of Classification Search
CPC ........... G01T 1/172; G01T 7/00; G01T 1/161; A61B 6/037
See application file for complete search history.

(56) References Cited

U.S. PATENT DOCUMENTS

| | | | |
|---|---|---|---|
| 2013/0334429 A1 | 12/2013 | Fukuchi et al. | ......... 250/363.03 |
| 2016/0291174 A1 | 10/2016 | Ishii | |
| 2017/0212254 A1 | 7/2017 | Gemba et al. | |

FOREIGN PATENT DOCUMENTS

| | | |
|---|---|---|
| JP | 2015-148448 A | 8/2015 |
| JP | 2015-190965 A | 11/2015 |
| JP | 2015-224986 A | 12/2015 |
| JP | 2016-035437 A | 3/2016 |
| WO | WO 2012/077468 A1 | 6/2012 |
| WO | WO 2015/146534 A1 | 10/2015 |

OTHER PUBLICATIONS

T. Tanimori et al., "An electron-tracking Compton telescope for a survey of the deep universe by MeV gamma-rays" The Astrophysical Journal, Aug. 26, 2015, vol. 810, No. 1, 28.

Tomono et al., "Environmental Gamma-Ray Imaging (V) With Electron-Tracking Compton Camera," [online], Sep. 28, 2015, the Physical Society 2016, from the Internet: http://www-cr.scphys.kyoto-u.ac.jp/research/MeV-gamma/Presentation/2015/JPS2015A_tomono20150915v5.pdf (color and handwritten signed grayscale files) (with English translation).

Sigma, Sigma Lens Catalogue, 2017, p. 17 with English translation.

International Preliminary Report on Patentability (Chapter I) dated Dec. 13, 2018 and Notification from the International Bureau (Form PCT/IB/326) in corresponding PCT International Application No. PCT/JP2017/019936 in Japanese.

International Preliminary Report on Patentability (Chapter I) dated Dec. 13, 2018 and Notification from the International Bureau (Form PCT/IB/338) in corresponding PCT International Application No. PCT/JP2017/019936 in English.

Extended European Search Report dated Mar. 23, 2020 in counterpart European Patent Application No. 17806614.8.

Shigeto Kabuki et al.: "Development of Electron Tracking Compton Camera using micro pixel gas chamber for medical imaging", Nuclear Instruments and Methods in Physics Research, Section A, vol. 580, No. 2 (2007) pp. 1031-1035, Elsevier BV * North-Holland, NL.

* cited by examiner

US 10,989,676 B2

GAMMA-RAY IMAGE ACQUISITION DEVICE AND GAMMA-RAY IMAGE ACQUISITION METHOD

CROSS-REFERENCE TO RELATED APPLICATIONS

The present application is a 35 U.S.C. §§ 371 national phase conversion of PCT/JP2017/019936, filed May 29, 2017, which claims priority to Japanese Patent Application No. 2016-107780, filed May 30, 2016, the contents of both of which are incorporated herein by reference. The PCT International Application was published in the Japanese language.

TECHNICAL FIELD

The present invention relates to a technique for acquiring a gamma-ray image.

BACKGROUND ART

Techniques for capturing the distribution of gamma-ray radiation as a two- or three-dimensional image have conventionally been studied in fields such as cosmic-ray observation and medical care. One method of detecting gamma-rays ranging from several hundred kilo electron volts (KeV) to several million electron volts (MeV) is to use scattering of gamma-rays resulting from the Compton effect. In Compton scattering, the incidence of a gamma-ray on a substance causes the emission of a recoil electron from the substance, and the incident gamma-ray turn into a scattered gamma-ray. To use Compton scattering to improve accuracy in detecting gamma-rays, techniques have been developed for detecting the direction and energy of each of a scattered gamma-ray and a recoil electron to acquire the direction of an incident gamma-ray. Such gamma-ray image acquisition devices are referred to as Electron-Tracking Compton Cameras (hereinafter, referred to as "ETCCs").

T. Tanimori et al., "An Electron-Tracking Compton Telescope for a Survey of the Deep Universe by MeV gamma-rays," Astrophysical Journal, The American Astronomical Society, Aug. 26, 2015, Volume 810, No. 1, 28 (hereinafter, referred to as "Document 1") have reported a technique for efficiently removing background radiation in cosmic-ray observation using an ETCC, after making various improvements thereto. Document 1 has also defined a Point Spread Function (hereinafter, referred to as "PSF") of the ETCC with improved performance, as in the case of ordinary optical telescopes, and has discussed resolving power quantitatively.

D. Tomono and other 17 members, "Environmental Gamma-Ray Imaging (V) With Electron-Tracking Compton Camera," [online], Sep. 28, 2015, the Physical Society of Japan, Retrieved Apr. 14, 2016, from the Internet: <http://www-cr.scphys.kyoto-u.ac.jp/research/MeV-gamma/Presentation/2015/JPS2015A_tomono20150915v5.pdf> have proposed a technique for imaging environmental gamma-rays with an ETCC. Japanese Patent Applications Laid-Open No. 2015-148448, No. 2015-190965, and No. 2015-224986 disclose techniques for improving the accuracy of an ETCC in tracking recoil electrons.

Meanwhile, in medical fields, Positron Emission Tomography (hereinafter, referred to as "PET") and Single Photon Emission Computed Tomography (hereinafter, referred to as "SPECT") perform focal imaging using gamma-rays.

Incidentally, in order to image the distribution of gamma-rays, conventional studies have focused on the removal of background radiation and the removal of noise generated in devices. Thus, no consideration is given to imaging for obtaining more useful information from obtained information. Besides, in PET, there is a limit to the reduction of noise because of the detection principles of PET.

SUMMARY OF INVENTION

The present invention is intended for a gamma-ray image acquisition device using Compton scattering. The gamma-ray image acquisition device includes a chamber, a scattered gamma-ray detector for detecting a target scattered gamma-ray generated by Compton scattering of an incident gamma-ray that enters the chamber from an external space, and acquiring a detected position and energy of the target scattered gamma-ray, a scattering position acquisition part for acquiring a scattering position of the incident gamma-ray in the chamber, a scattering direction acquisition part for acquiring a direction of the target scattered gamma-ray on the basis of the scattering position and the detected position, a recoil electron information acquisition part for acquiring a direction and energy of a recoil electron recoiling from the scattering position, an incident gamma-ray calculator for acquiring an incident direction and energy of the corresponding incident gamma-ray from the direction and energy of the target scattered gamma-ray and the direction and energy of the recoil electron, and an image acquisition part for acquiring a two-dimensional image by imaging spectroscopy based on incident directions and energies of a plurality of incident gamma-rays, the two-dimensional image being an image in which each pixel corresponding to the incident direction of incident gamma-rays includes energy distribution information.

In the two-dimensional image, an area and a solid angle of an imaging range are proportional to each other, and a full width at half maximum of a point spread function that indicates accuracy of the incident direction acquired by the incident gamma-ray calculator corresponds to a visual angle less than or equal to 15 degrees.

Since the area and the solid angle of the imaging range in the two-dimensional image are proportional to each other, an image that indicates more useful information than conventional images can be acquired from the information obtained by the gamma-ray image acquisition device.

In a preferred embodiment, the image acquisition part identifies at least either ones of direct incident gamma-rays and scattered incident gamma-rays from among the plurality of incident gamma-rays and acquiring a distribution of the incident directions of the at least either gamma-rays as a two-dimensional image, the direct incident gamma-rays directly entering the chamber from a radiation source, and the scattered incident gamma-rays falling within an energy range lower than an energy range of the direct incident gamma-rays.

A gamma-ray image acquisition device according to another embodiment includes a chamber, a scattered gamma-ray detector for detecting a target scattered gamma-ray generated by Compton scattering of an incident gamma-ray that enters the chamber from an external space, and acquiring a detected position and energy of the target scattered gamma-ray, a scattering position acquisition part for acquiring a scattering position of the incident gamma-ray in the chamber, a scattering direction acquisition part for acquiring a direction of the target scattered gamma-ray on the basis of the scattering position and the detected position, a recoil electron information acquisition part for acquiring a direction and energy of a recoil electron recoiling from the scattering position, an incident gamma-ray calculator for acquiring an incident direction and energy of the corresponding incident gamma-ray from the direction and energy of the target scattered gamma-ray and the direction and energy of the recoil electron, and an image acquisition part for identifying first incident gamma-rays falling within a first energy range and second incident gamma-rays falling within a second energy range different from the first energy range from among a plurality of incident gamma-rays, acquiring a first gamma-ray image that indicates a three-dimensional gamma radiation field from information on the first incident gamma-rays, and acquiring a second gamma-ray image that indicates a three-dimensional gamma radiation field from information on the second incident gamma-rays.

A full width at half maximum of a point spread function that indicates accuracy of the incident direction acquired by the incident gamma-ray calculator corresponds to a visual angle less than or equal to 15 degrees.

By identifying the first incident gamma-rays falling within the first energy range and the second incident gamma-rays falling within the second energy range different from the first energy range, the first gamma-ray image and the second gamma-ray image that indicate useful information can be acquired from the information obtained by the gamma-ray image acquisition device.

In a preferred embodiment, the first incident gamma-rays are direct incident gamma-rays that directly enter the chamber from a radiation source, and the second incident gamma-rays are scattered incident gamma-rays that fall within an energy range lower than an energy range of the direct incident gamma-rays.

In a preferable example, the incident gamma-rays are emitted from an object that contains a radioactive material. In further preferable example, the object is a human body to which a drug that emits positrons or gamma-rays is administered.

In another preferred embodiment, the gamma-ray image acquisition device further includes a storage for storing an electron density distribution in the object, provided in advance, and a corrector for correcting the first gamma-ray image by using the second gamma-ray image and the electron density distribution.

In yet another preferred embodiment, the gamma-ray image acquisition device further includes an electron density distribution acquisition part for smoothing the first gamma-ray image and acquiring an electron density distribution in the object from the first gamma-ray image that has been smoothed and the second gamma-ray image.

Preferably, the gamma-ray image acquisition device further includes an attachment part for installing an additional chamber same as the chamber.

A gamma-ray image acquisition device according to yet another preferred embodiment includes a chamber that some of paired gamma-rays generated by electron-positron pair annihilation occurring in an object enter, each as an incident gamma-ray, the object containing a substance that emits positrons, a scattered gamma-ray detector for detecting a target scattered gamma-ray generated by Compton scattering of the incident gamma-ray in the chamber and acquiring a detected position and energy of the target scattered gamma-ray, a scattering information acquisition part for acquiring a scattering position and scattering time of the incident gamma-ray in the chamber, a scattering direction acquisition part for acquiring a direction of the target scattered gamma-ray on the basis of the scattering position and the detected position of the target scattered gamma-ray, a recoil electron information acquisition part for acquiring a direction and energy of a recoil electron recoiling from the scattering position, an incident gamma-ray calculator for acquiring an incident direction and energy of the corresponding incident gamma-ray from the direction and energy of the target scattered gamma-ray and the direction and energy of the recoil electron, a counter detector disposed on a side opposite to the chamber with the object therebetween, and for acquiring a detected position and detected time of a gamma-ray that enters from the object, a paired gamma-ray identification part for identifying, from among the gamma-rays detected by the counter detector, a gamma-ray that has the detected position and detected time of a gamma-ray generated in a pair with an incident gamma-ray that enters the chamber, on the basis of the incident direction, energy, scattering position, and scattering time of the incident gamma-ray, a paired gamma-ray generated position acquisition part for acquiring a generated position, in the object, of the paired gamma-rays identified by the paired gamma-ray identification part, on the basis of the scattering position and scattering time of one of the paired gamma-rays in the chamber and the detected position and detected time of the other of the paired gamma-rays detected by the counter detector, and an image acquisition part for acquiring generated positions of a plurality of paired gamma-rays as a three-dimensional image.

A full width at half maximum of a point spread direction that indicates accuracy of the incident direction acquired by the incident gamma-ray calculator corresponds to a visual angle less than or equal to 15 degrees.

Providing the counter detector allows the generated position of the paired gamma-rays to be acquired at low cost and with high accuracy.

Preferably, the counter detector includes a lead-containing plastic scintillator or a lead-containing glass scintillator.

In a preferred embodiment, the gamma-ray image acquisition device further includes another chamber same as the chamber, and a configuration of acquiring a generated position of paired gamma-rays from information on scattering of an incident gamma-ray that enters the another chamber and information on a gamma-ray that is incident on the counter detector, as in the case of the chamber. An angle formed by a direction from the chamber to the object and a direction from the another chamber to the object is greater than or equal to 0 degrees and less than or equal to 140 degrees.

The present invention is also intended for a gamma-ray image acquisition method of acquiring a gamma-ray image.

These and other objects, features, aspects and advantages of the present invention will become more apparent from the following detailed description of the present invention when taken in conjunction with the accompanying drawings.

DESCRIPTION OF EMBODIMENTS

Figure 1:
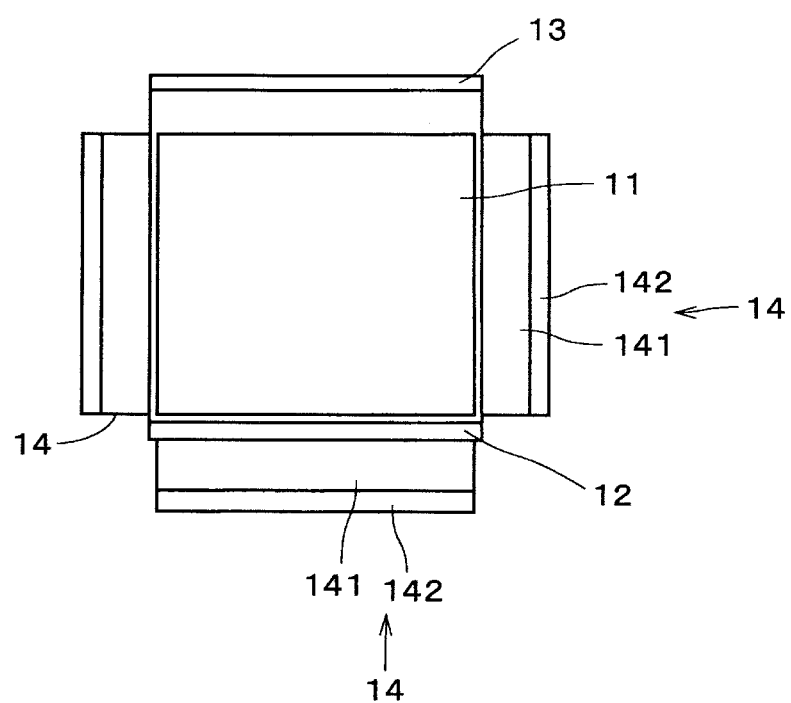
FIG. 1 illustrates a detector.

FIG. 1 illustrates a detector 10 of a gamma-ray image acquisition device according to a preferred embodiment of the present invention. The gamma-ray image acquisition device is an electron-tracking Compton camera (ETCC) using Compton scattering. The basic structure of the detector 10 is similar to that disclosed in the aforementioned Non-Patent Document 1. The detector 10 includes a chamber 11 called a Time Projection Chamber (TPC) in the center. The chamber 11 has a rectangular parallelepiped shape, with its interior filled with a gas. The gas in the chamber 11 is, for example, a gas that contains argon as its primary component. Other gases may be added as appropriate to this gas. Alternatively, the gas may be other than an argon gas. The internal pressure of the chamber 11 is, for example, in the range of one to several atmospheres.

Gamma rays enter the chamber 11 from various directions. Hereinafter, gamma-rays that enter the chamber 11 from an external space are referred to as "incident gamma-rays." Some of the incident gamma-rays interact with electrons of atoms in the gas within the chamber 11, causing Compton scattering. The Compton scattering changes the travel directions of the incident gamma-rays, and the incident gamma-rays turn into scattered gamma-rays. A gamma-ray that corresponds to one Compton scattering event is one photon. Hereinafter, the scattered gamma-ray generated by the Compton scattering of the incident gamma-ray is referred to as "a target scattered gamma-ray." The electron that has received energy from the incident gamma-ray is emitted as a recoil electron from the atom. In this way, a region within the chamber 11 serves as a scattering region for detecting gamma-rays.

At the bottom of the chamber 11, a two-dimensional gas amplification position detector 12 is provided. One example of the two-dimensional gas amplification position detector 12 is a Micro Pixel Chamber (μPIC). The two-dimensional gas amplification position detector 12 according to the present embodiment is a sort of micro pattern gas detector (MPGD) and acquires the incident positions of charged particles. A drift plane 13 is provided above the chamber 11. In the chamber 11, an electric field is formed from the two-dimensional gas amplification position detector 12 toward the drift plane 13. The recoil electrons ionize electrons in the gas within the chamber 11, forming an electron cloud. The electron cloud is guided to the two-dimensional gas amplification position detector 12 by the electric field, and detected.

A scattered gamma-ray detector 14 is provided on each of the four outer side faces of the chamber 11 and on the lower side of the two-dimensional gas amplification position detector 12. The scattered gamma-ray detectors 14 each include a scintillator array 141 of two-dimensionally arranged scintillators, and a detection circuit 142 that detects fluorescence from each scintillator. Various types of materials are usable as the scintillators, and for example, a material that contains gadolinium silicate (GSO) is used. The scintillator array 141 is located between the chamber 11 and the detection circuit 142. When a target scattered gamma-ray scattered from the chamber 11 is absorbed by one of the scintillators, the detection circuit 142 detects light emitted from that scintillator to acquire the detected position of the target scattered gamma-ray. Note that the scattered gamma-ray detector 14 may be provided on only the bottom of the chamber 11. The four scattered gamma-ray detectors 14 provided on the side faces are effective for improving detection efficiency.

Figure 2:
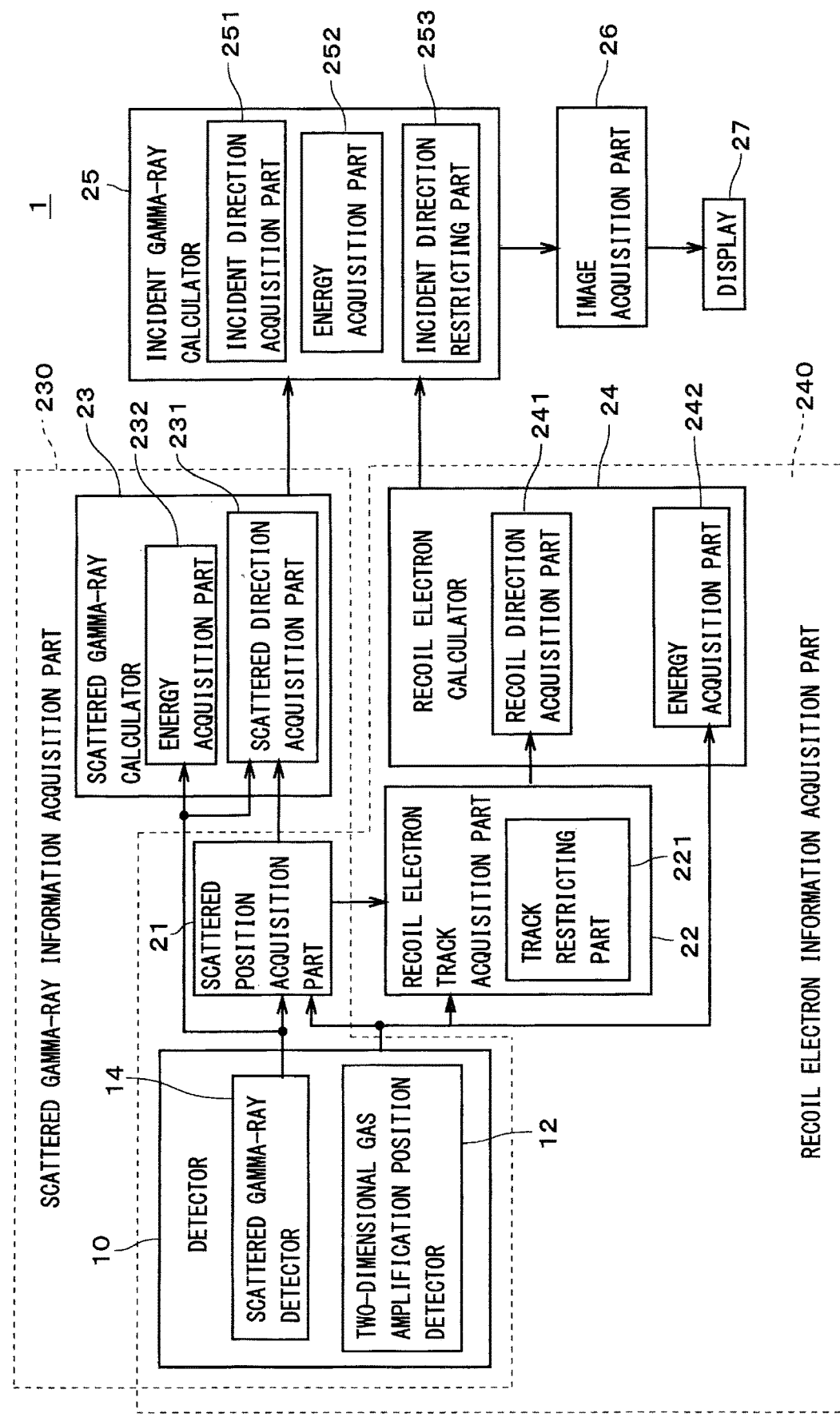
FIG. 2 is a block diagram illustrating a configuration of a gamma-ray image acquisition device.

FIG. 2 is a block diagram illustrating a configuration of a gamma-ray image acquisition device 1. The gamma-ray image acquisition device 1 includes the detector 10, a scattering position acquisition part 21, a recoil electron track acquisition part 22, a scattered gamma-ray calculator 23, a recoil electron calculator 24, an incident gamma-ray calculator 25, an image acquisition part 26, and a display 27. The scattering position acquisition part 21, the recoil electron track acquisition part 22, the scattered gamma-ray calculator 23, the recoil electron calculator 24, the incident gamma-ray calculator 25, and the image acquisition part 26 are implemented by dedicated electrical circuits, general-purpose computing circuits, or a combination of these circuits.

Figure 3:
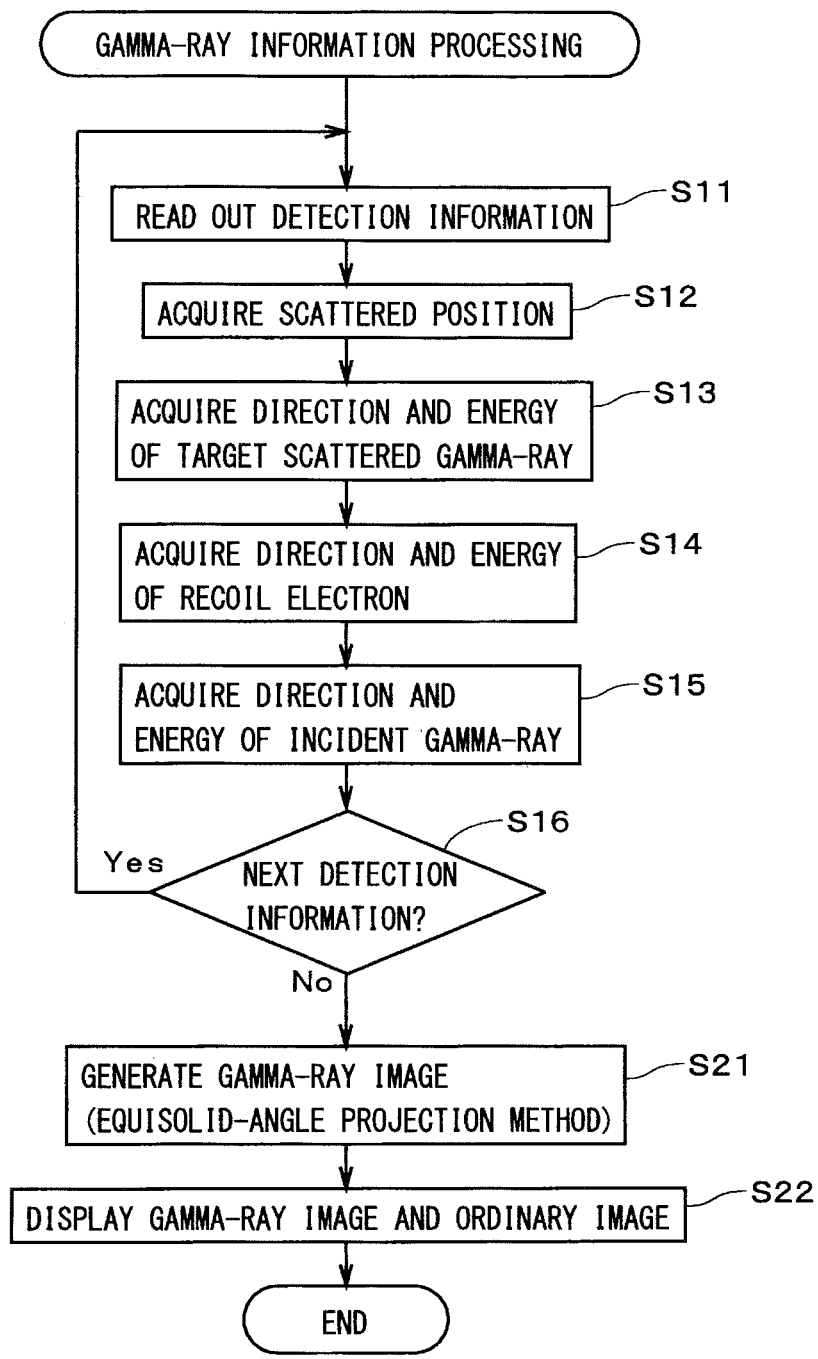
FIG. 3 illustrates a procedure of operations of the gamma-ray image acquisition device.
Figure 4:
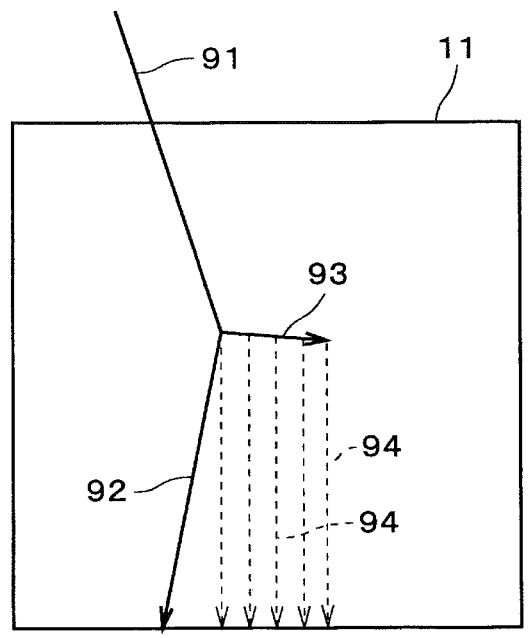
FIG. 4 illustrates how Compton scattering occurs in a chamber.

FIG. 3 illustrates a procedure of operations of the gamma-ray image acquisition device 1. The procedure is based on the assumption that, prior to the operations illustrated in FIG. 3, there is a step of causing an incident gamma-ray to enter the chamber 11 from an external space to acquire detection information thereon. FIG. 4 illustrates how Compton scattering occurs in the chamber 11. As described previously, the Compton scattering causes a target scattered gamma-ray 92 and a recoil electron 93 to be derived from an incident gamma-ray 91. In practice, the target scattered gamma-ray 92 may further induce Compton scattering, but in the present embodiment, such a complicated case is omitted in order to simplify description.

When the target scattered gamma-ray 92 has entered one of the five scattered gamma-ray detectors 14 (see FIG. 1), the scattered gamma-ray detector 14 acquires the detected position and detected time of the target scattered gamma-ray 92. On the other hand, the recoil electron 93 ionizes electrons of atoms in the gas within the chamber 11 as described previously and travels while losing its energy. An electron cloud of ionization electrons 94 is moved, by the electric field, toward the two-dimensional gas amplification position detector 12 (see FIG. 1) provided at the bottom of the chamber 11, as indicated by broken-line arrows in FIG. 4. The two-dimensional gas amplification position detector 12 includes two-dimensionally arranged micro detectors. Each micro detector detects an incoming ionization electron 94. In this way, the detected positions and detected times of the ionization electrons 94 are acquired. Detection information on the target scattered gamma-ray 92 and the ionization electrons 94 is stored in a memory, which is not shown in FIG. 2. Every time the target scattered gamma-ray 92 is detected, the detection information is accumulated in the memory.

The scattering position acquisition part 21 reads out detection information on the initially stored target scattered gamma-ray 92 and detection information on the corresponding electron cloud (step S11). Hereinafter, these pieces of information are collectively and simply referred to as "detection information." The scattering position acquisition part 21 identifies an initially formed part of the electron cloud. The scattering position acquisition part 21 then obtains a drift distance of the initial ionization electron 94 in the electric field on the basis of the amount of time from when the target scattered gamma-ray 92 is detected to when the initial ionization electron 94 is detected. That is, the height from the two-dimensional gas amplification position detector 12 to a scattering position is acquired. The information on the initial ionization electron 94 includes the two-dimensional position thereof in the two-dimensional gas amplification position detector 12. Thus, ultimately the scattering position is acquired as information on the three-dimensional position in the chamber 11 (step S12).

The recoil electron track acquisition part 22 obtains the three-dimensional shape of the electron cloud on the basis of the information on the ionization electrons 94, which is detected over time by the two-dimensional gas amplification position detector 12. At this time, the position of the electron cloud in the chamber 11 is also determined by reference to the information on the scattering position. Accordingly, the track of the recoil electron 93 is acquired. Here, a track restricting part 221 of the recoil electron track acquisition part 22 determines whether the recoil electron 93 has collided with the side or bottom face of the chamber 11. In the case of collision, the detection information obtained from the Compton scattering event of interest is excluded from targets for subsequent arithmetic operations.

The scattered gamma-ray calculator 23 includes a scattering direction acquisition part 231 and an energy acquisition part 232. The scattering direction acquisition part 231 acquires the direction of the target scattered gamma-ray 92 on the basis of the scattering position and the detected position of the target scattered gamma-ray 92. The energy acquisition part 232 acquires the energy of the target scattered gamma-ray 92 on the basis of the magnitude of a detection signal output from the scattered gamma-ray detector 14 (step S13). It may be perceived that the energy of the target scattered gamma-ray 92 is substantially acquired by the scattered gamma-ray detector 14.

The recoil electron calculator 24 includes a recoil direction acquisition part 241 and an energy acquisition part 242. The recoil direction acquisition part 241 acquires the recoil direction of the recoil electron 93 on the basis of the shape of the electron cloud in the vicinity of the scattering position. The energy acquisition part 242 acquires the energy of the recoil electron 93 on the basis of the size and length of the electron cloud (step S14).

As described above, the detector 10, the scattering position acquisition part 21, and the scattered gamma-ray calculator 23 function as a scattered gamma-ray information acquisition part 230 for acquiring the direction and energy of the target scattered gamma-ray 92. The detector 10, the scattering position acquisition part 21, the recoil electron track acquisition part 22, and the recoil electron calculator 24 function as a recoil electron information acquisition part 240 for acquiring the direction and energy of the recoil electron 93.

The incident gamma-ray calculator 25 includes an incident direction acquisition part 251, an energy acquisition part 252, and an incident direction restricting part 253. The incident direction acquisition part 251 uses the Compton scattering formula to obtain an incident direction, i.e., incoming direction, in which the corresponding incident gamma-ray 91 enters the detector 10, on the basis of the scattering direction and energy of the target scattered gamma-ray 92 and the recoil direction and energy of the recoil electron 93. Note that the scattering direction, the recoil direction, and the incident direction are vector information in arithmetic operations.

Figure 5:
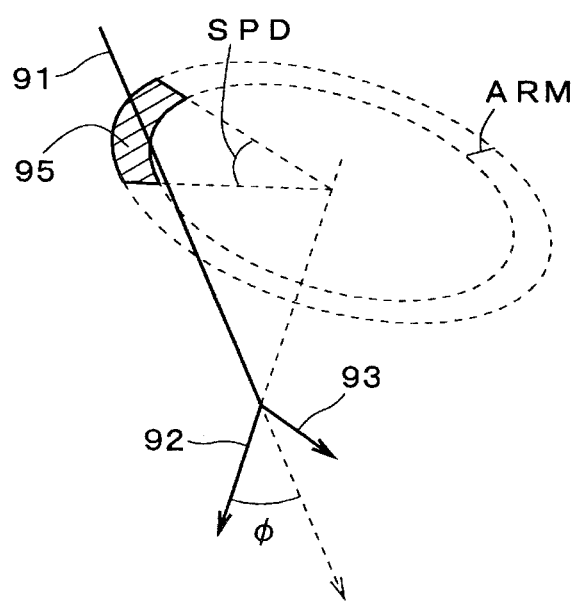
FIG. 5 is a diagram for describing an ARM and an SPD.

In the gamma-ray image acquisition device 1, accuracy or angular resolution in determining a scattering angle φ formed by the direction of the target scattered gamma-ray 92 and the incident direction of the incident gamma-ray 91 is referred to as the Angular Resolution Measure (ARM). As illustrated in FIG. 5, the ARM is expressed as the width of a circular ring-shaped region in a plane perpendicular to the direction of the target scattered gamma-ray 92. On the other hand, accuracy or angular resolution in determining a scattering plane that is a plane determined by a vector indicating the scattering direction of the target scattered gamma-ray 92 and a vector indicating the recoil direction of the recoil electron 93 is referred to as the Scatter Plane Deviation (SPD). The SPD narrows down the aforementioned circular ring-shaped region in the angular direction. For one piece of detection information, the ARM and the SPD derive a diagonally hatched region 95 in FIG. 5 as a conceivable range of the actual incident direction of the incident gamma-ray 91.

The energy acquisition part 252 acquires the energy of the incident gamma-ray 91 on the basis of the fact that a sum of the energy of the target scattered gamma-ray 92 and the energy of the recoil electron 93 is equal to a sum of the energy of the incident gamma-ray 91 and the energy of an electron regarded as a resting electron, according to the law of conservation of energy (step S15).

Incidentally, the gamma-ray image acquisition device 1 acquires the incident direction of the incident gamma-ray 91 with high accuracy. Thus, the concept of the Point Spread Function (PSF) can be introduced as an index that indicates the accuracy of the incident direction, as in the case of ordinary telescopes. The full width at half maximum of the PSF can be used as the resolution of the gamma-ray image acquisition device 1.

The PSF can be obtained through actual measurements or simulations using the above-described ARM and SPD. For example, a radiation source that can be regarded as a point is disposed at a considerable distance, and the incident direction of an incident gamma-ray is obtained and plotted every time the incident gamma-ray is detected, so as to acquire the PSF from the distribution of the incident directions. In the case of obtaining the PSF through simulations, the incident direction of each incident gamma-ray emitted from a virtual radiation source is obtained after being changed stochastically and randomly using the ARM and the SPD. Then, the PSF is acquired from the distribution of a large number of incident directions obtained by arithmetic operations.

The full width at half maximum of the PSF of the gamma-ray image acquisition device 1 corresponds to a visual angle less than or equal to 15 degrees. Preferably, the visual angle corresponding to the full width at half maximum is less than or equal to 10 degrees, more preferably less than or equal to 7 degrees, and yet more preferably less than or equal to 3 degrees. Theoretically, the visual angle corresponding to the full width at half maximum is greater than or equal to one degree. The same applied to other embodiments described below.

The incident direction restricting part 253 of the incident gamma-ray calculator 25 excludes, from among the incident directions acquired in step S15, gamma-rays that enter the detector 10 from regions outside a to-be-observed range. Accordingly, most of incident gamma-rays that enter as background noise or other noise generated from scattered gamma-rays or the like are excluded from the incident gamma-rays 91 that are to be detected.

When processing of one piece of detection information is completed, it is determined whether there is a next piece of detection information (step S16). If there is a next piece of detection information, steps S11 to S15 described above are repeated for the next piece of detection information. Accordingly, the incident directions and energies of a large number of incident gamma-rays 91 are acquired. The incident directions and energies of the incident gamma-rays 91 are hereinafter referred to as "incident gamma-ray information."

The image acquisition part 26 generates a gamma-ray image that is a two-dimensional image from the incident gamma-ray information (step S21). To be precise, the image acquisition part 26 generates data on the gamma-ray image. The gamma-ray image has a lower resolution than ordinary images, so that one pixel in the gamma-ray image corresponds to a region of a certain size in an ordinary image. Hereinafter, pixels in the gamma-ray image are expressed as "pixel regions." For example, the length of one side of a pixel region in the center of the image corresponds to the full width at half maximum of the PSF. Each pixel region corresponds to the incident direction of incident gamma-rays.

The gamma-ray image is generated by an equisolid-angle projection method. That is, in the two-dimensional image, the area and the solid angle of the imaging range are proportional to each other. The display 27 displays an ordinary image and a gamma-ray image that are obtained by the equisolid-angle projection method (step S22). These images may be displayed side by side, or may be displayed overlapping each other.

The gamma-ray image also includes the energy distribution of a plurality of incident gamma-rays corresponding to each pixel region, i.e., spectrum information. In this way, the two-dimensional gamma-ray image is acquired by imaging spectroscopy based on the incident directions and energies of a plurality of incident gamma-rays. Gamma-rays that directly enter from a radiation source appear as peaks in the spectrum.

Here, the image acquisition part 26 can also extract incident gamma rays that fall within a specific energy range from among the incident gamma-rays corresponding to each pixel region, and can generate a gamma-ray image that uses the number of extracted incident gamma rays to express the densities of the pixel regions. Therefore, the distribution of a specific radioactive material can be acquired by setting in the image acquisition part 26 an energy range of nuclear gamma-rays that directly enter from the radioactive material.

On the other hand, a gamma-ray image that indicates the occurrence of some sort of phenomenon caused by a radioactive material can be acquired by setting in the image acquisition part 26 an energy range of scattered gamma-rays that enter the detector 10 after gamma-rays emitted from the radioactive material are scattered in a surrounding substance. For example, in the case where there is an outflow of groundwater contaminated with a radioactive material, regions where large amounts of scattered gamma-rays different from atmospheric scattered gamma-rays are detected appear in the gamma-ray image.

In other words, the image acquisition part 26 identifies at least either ones of direct incident gamma-rays and scattered incident gamma rays from among a plurality of incident gamma-rays and acquires the distribution of the incident directions of the at least either gamma-rays as a two-dimensional image. The direct incident gamma-rays fall within an energy range of gamma-rays that directly enter the chamber 11 of the detector 10 from a radiation source, and the scattered incident gamma-rays fall within an energy range lower than the energy range of direct incident gamma-rays.

In this way, the conditions of gamma-rays in surroundings can be grasped more precisely by acquiring a gamma-ray image that restricts the energy range of incident gamma-rays or, more preferably, by acquiring a plurality of gamma-ray images that indicate different energy ranges.

Figure 6A:
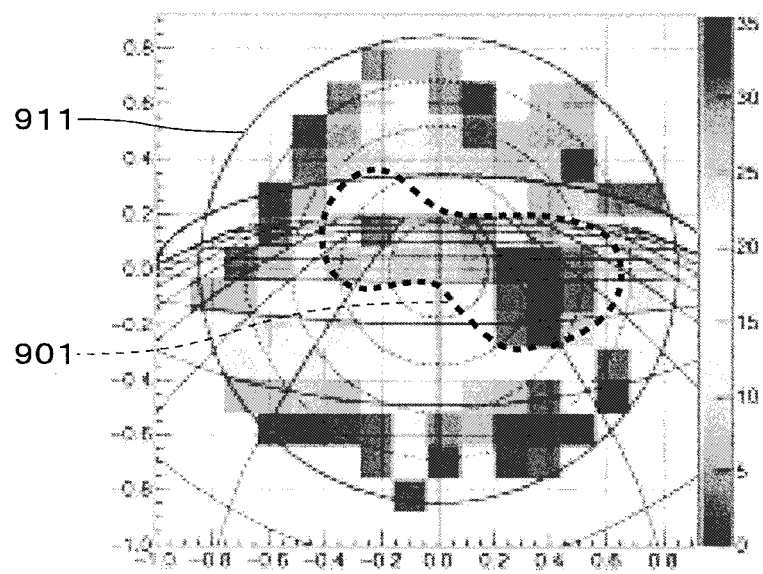
FIG. 6A illustrates an example of a gamma-ray image acquired by an equisolid-angle projection method.
Figure 6B:
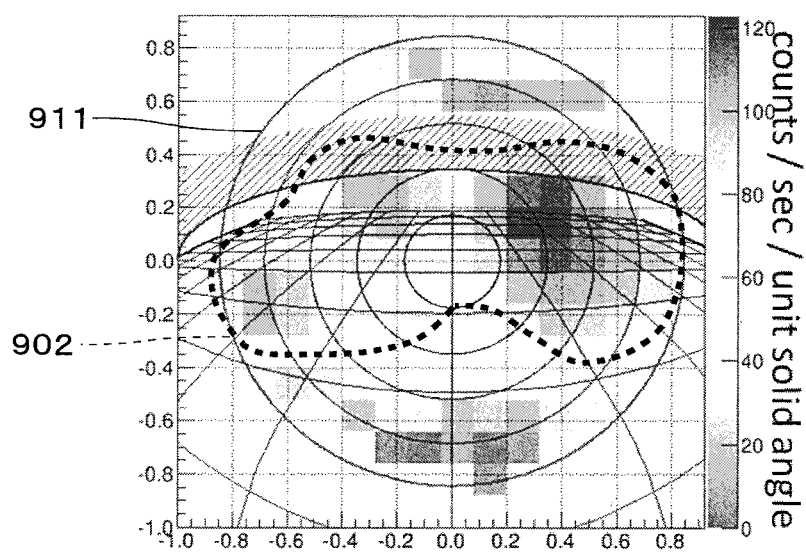
FIG. 6B illustrates an example of a conventional gamma-ray image.

FIG. 6A illustrates an example of the gamma-ray image acquired by the equisolid-angle projection method. FIG. 6A illustrates an image of a region that has undergone decontamination for removing a radioactive material. FIG. 6B illustrates a conventional gamma-ray image obtained from the same incident gamma-ray information. Each gamma-ray image is an image in which square pixel regions are arranged two-dimensionally. Circles 911 correspond to a visual angle of 50°. The conventional gamma-ray image has poor accuracy in the incoming directions of gamma-rays, and has more leaks in each pixel region than in the image obtained by the equisolid-angle projection method because incoming positions are just simply plotted on a virtual plane. Therefore, FIG. 6A shows a large number of gamma-rays detected in a region 901 enclosed by the broken line, whereas FIG. 6B shows a large number of gamma-rays detected in a wide region 902 enclosed by the broken line.

Figure 6C:
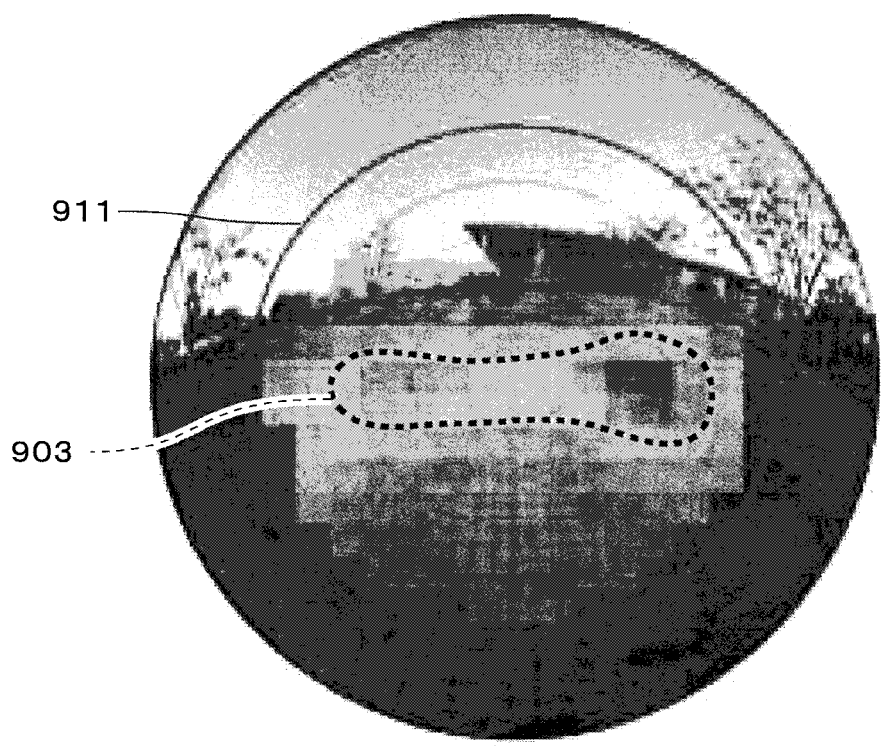
FIG. 6C illustrates an example of a gamma-ray image produced from doses measured by an environmental radiation monitor.

In FIG. 6A, the imaging ranges corresponding to each pixel region have the same solid angle. FIG. 6C illustrates an image obtained by measuring doses of gamma rays at a height of 10 cm from the ground in many locations with an environmental radiation monitor (PA-1100 produced by HORIBA, Ltd.) and converting the measured doses into gamma-ray intensity per equisolid angle. In FIG. 6C, a natural image showing the actual environment is converted and overlaid onto the equisolid angle projection. FIG. 6C shows a large number of gamma-rays detected in a region 903 enclosed by the broken line. The gamma-ray image in FIG. 6A matches more closely with the actual measurement results than the conventional gamma-ray image in FIG. 6B.

Figures 7A, 7B:
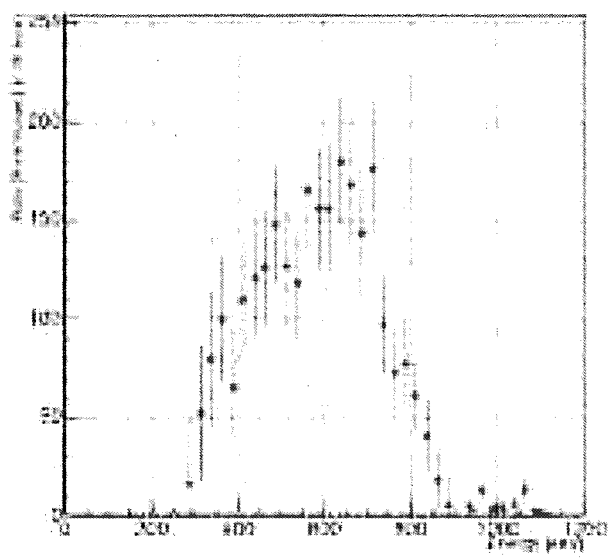
FIG. 7A illustrates a spectrum of gamma-rays coming from the ground.
FIG. 7B illustrates a spectrum of gamma-rays coming from the sky.

FIG. 7A illustrates a spectrum of energies of gamma-rays coming from the ground below a horizontal line 912 within a circle 911 illustrated in FIG. 8. FIG. 7B illustrates a spectrum of energies of gamma-rays coming from the sky above the horizontal line 912 within the circle 911. As can be seen from these figures, the spectrum of the gamma-rays coming from the sky and the spectrum of the gamma-rays coming from the ground are clearly different because the PSF of the gamma-ray image acquisition device 1 has a small extent.

Figure 7C:
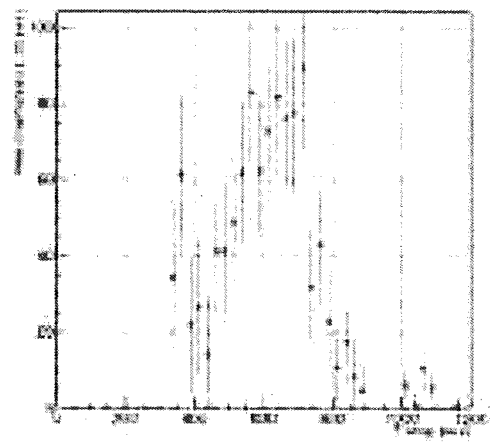
FIG. 7C illustrates a spectrum in a region decontaminated insufficiently.
Figure 7D:
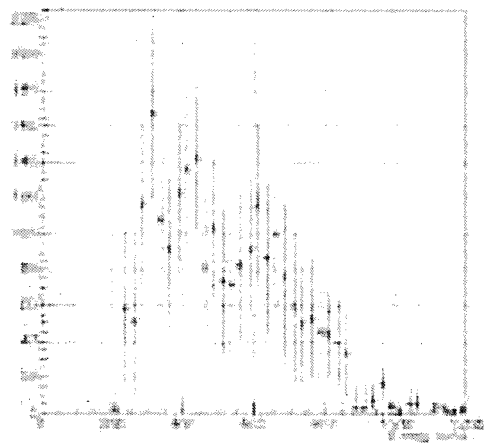
FIG. 7D illustrates a spectrum in a region decontaminated to a sufficient level.
Figure 8:
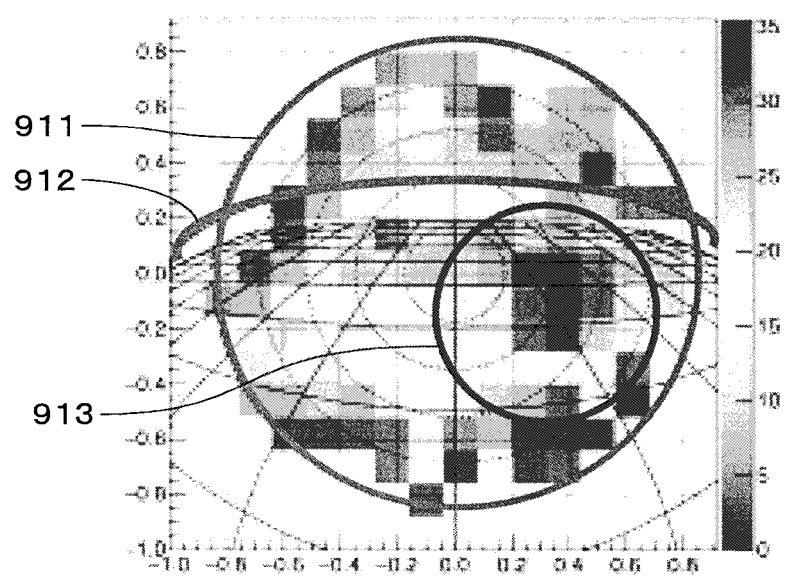
FIG. 8 illustrates a region decontaminated insufficiently.

FIG. 7C illustrates a spectrum of energies within a circle 913 illustrated in FIG. 8. FIG. 7D illustrates a spectrum of energies within a region of the ground other than the circle 913. FIG. 7C shows the presence of a peak at 662 keV, which indicates the presence of radioactive cesium, but FIG. 7D shows no peak at 662 keV. This indicates that the region indicated by the circle 913 is insufficiently decontaminated. With conventional techniques, measurement that involves time-consuming movement of a device is required in order to acquire regions where radioactive materials exist. In contrast, the gamma-ray image acquisition device 1 whose PSF has a small extent can easily acquire regions where radioactive materials exist over a wide range, as in the case of capturing an ordinary image. Note that although the spectrums are obtained for each region in FIGS. 7A to 7D, spectrums may be acquired for each pixel region as described previously.

By using the equisolid-angle projection method, the distribution of gamma-ray intensities is measured (the gamma-ray intensities indicating intensities defined in astronomy, i.e., the number of gamma-rays per unit area, per unit time, or per unit solid angle). These intensities (bundles of gamma-rays) are maintained per solid angle. Thus, information is maintained irrespective of distance and made invariant. This is the factor that enables imaging nuclear spectroscopy. Since the information on gamma-rays does not change at infinity within the range of resolving power depending on the PSF, measurement similar to that of luminous intensities, referred to in optics, is made possible. The luminous intensities refer to amounts that include physical information on a light-emitting source of light at infinity.

Accordingly, in the case of gamma-rays, the density of quantitative radiation from a radiation source can be measured irrespective of distance. As a result, even if the distances between the points of radiation of gamma-rays and the detector 10 are unknown, radiation intensity per unit area can be measured at the points of radiation, and even gamma-ray radiation intensities at considerable distances can be measured. The gamma-ray image acquisition device 1 has a wide field of view, and thus can capture a wide-area distribution of gamma-rays beyond the range visible by human eyes. Thus, the equisolid-angle projection method is particularly suitable.

For example, if the gamma-ray image acquisition device 1 is carried up in the sky to detect gamma-rays emitted from the Earth's surface, a wide-area distribution of the quantities of radioactive nuclides on the Earth's surface can be visualized quantitatively. In nuclear-related facilities, wide-range quantitative imaging of gamma-ray radiation intensities (which can be regarded as equivalent to the quantities of radioactive nuclides) can help forestalling accidents, and also improves the ability to respond to the occurrence of accidents. For example, in case of occurrence of an accident, a three-dimensional distribution of radiation doses emitted from a nuclear reactor and the directions of diffusion can be measured for each nuclear species. This enables speedy evacuation planning in conjunction with a diffusion prediction system such as the System for Prediction of Environmental Emergency Dose Information (SPEEDI).

The safety of occupations that use radiation is improved dramatically, and the efficiency thereof is also improved significantly. For example, the capability to measure the quantities of radioactive nuclides existing on the Earth's surface, walls, or other places makes it possible to predict where to decontaminate first and how the radiation doses will change by the decontamination. This improves the efficiency of decontamination of places contaminated by radioactive materials. In leakage monitoring conducted in, for example, contaminated water tanks or storage facilities, it is possible to find leakage at the initial stage and to accurately identify the location of the leakage. In decommissioning of a nuclear reactor, the capability to measure the intensities of radiation emitted from substances around the reactor core makes it possible to systematically determine a decommissioning procedure by simulations. Therefore, significant improvements in efficiency and safety can be expected.

As described above, with use of the equisolid-angle projection method, an image that indicates more useful information than conventional images can be acquired from the information obtained by the gamma-ray image acquisition device 1.

Figure 9:
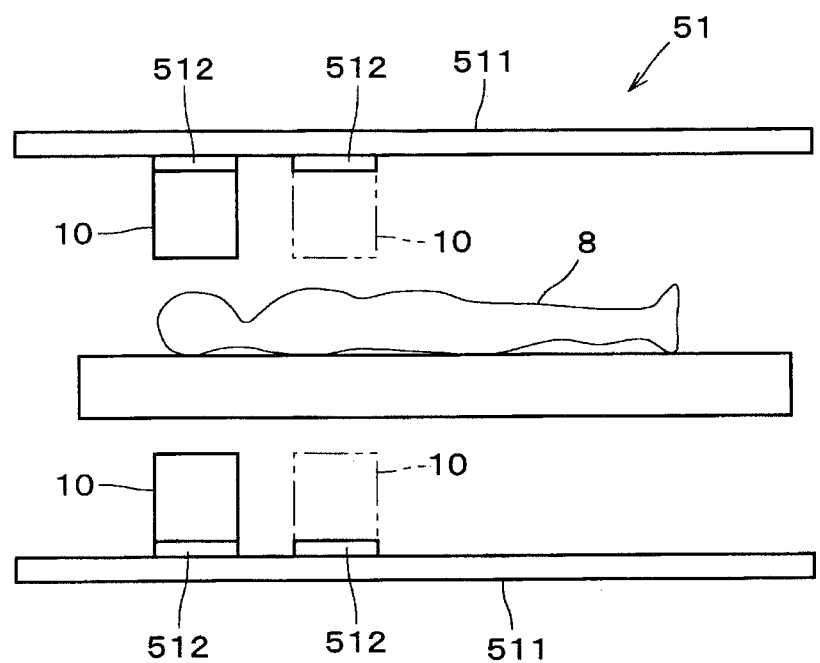
FIG. 9 illustrates the arrangement of detectors relative to a patient.

The next description is on examples of using the gamma-ray image acquisition device 1 for medical purposes. FIG. 9 illustrates the arrangement of detectors 10, viewed from one side of a patient 8 who is lying on his or her back to be examined. In the example in FIG. 9, two detectors 10 are arranged above and below the patient 8, with the head of the patient 8 therebetween. The gamma-ray image acquisition device 1 is provided with a mover 51 that moves the two detectors 10 in parallel with the axis of the trunk of the patient 8. The mover 51 includes a guide 511 that extends in parallel with the axis of the trunk above the patient 8, and another guide 511 that extends in parallel with the axis of the trunk below the patient 8. Each guide 511 is provided with an attachment part 512, and the attachment part 512 moves along the guide 511. The detectors 10 are attached to the attachment parts 512 so that each detector 10 can move along the guide 511.

Each guide 511 is also provided with another attachment part 512 to which no detector 10 is attached. When installing an additional detector 10 having the same structure as that of each detector 10 including the chamber 11, this attachment part 512 is used to attach the additional detector 10. If two additional detectors 102 are installed, the gamma-ray image acquisition device 1 can use two pairs of detectors 10.

As in the case of PET, a drug that contains a radioactive material that emits positrons is administered to the patient 8, i.e., a human body. The radioactive material is gathered at an affected part, and gamma-rays generated by positron annihilation enter the detectors 10 as incident gamma-rays. Of course, a drug that contains a radioactive material that emits gamma-rays may be used, as in the case of SPECT.

Figure 10:
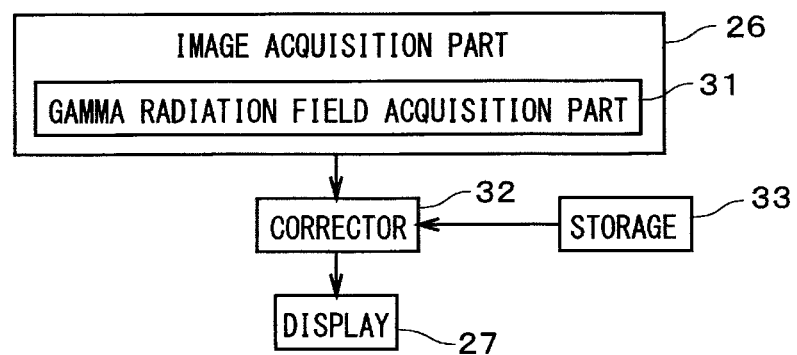
FIG. 10 illustrates some constituent elements of the gamma-ray image acquisition device.
Figure 11:
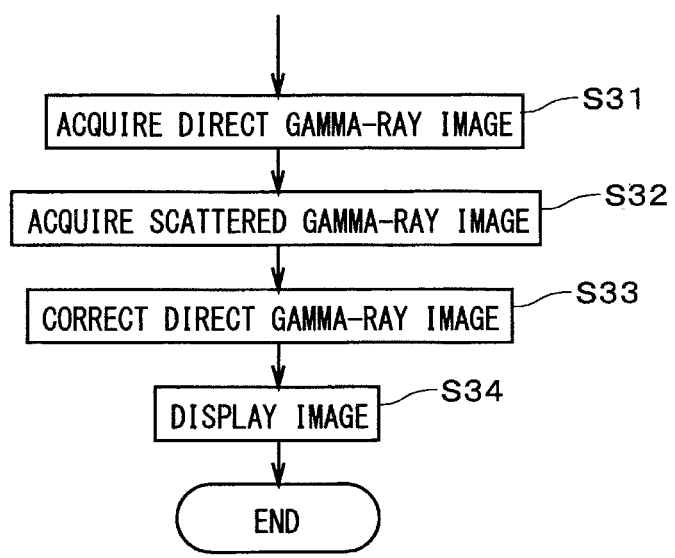
FIG. 11 illustrates some operations of the gamma-ray image acquisition device.

FIG. 10 illustrates constituent elements that are added to the gamma-ray image acquisition device 1 in FIG. 2. The image acquisition part 26 includes a gamma radiation field acquisition part 31. A corrector 32 is additionally provided between the image acquisition part 26 and the display 27, and a storage 33 is connected to the corrector 32. FIG. 11 illustrates processing that is performed after step S16 in FIG. 3.

The image acquisition part 26 receives input of the directions, energies, and scattering positions of incident gamma-rays detected by the two upper and lower detectors 10. The image acquisition part 26 references the energies of the incident gamma-rays and identifies direct incident gamma-rays and scattered incident gamma-rays. The direct incident gamma-rays are nuclear gamma-rays that directly enter the detectors 10 from a radiation source. For example, the direct incident gamma-rays have energies of around 511 keV. The energy range of the direct incident gamma-rays is appropriately set depending on the accuracy in detecting the energies of the gamma-rays. The scattered incident gamma-rays are gamma-rays that fall within an energy range lower than the energy range of the direct incident gamma-rays. For example, the scattered incident gamma-rays fall within an energy range higher than or equal to 100 keV and less than or equal to the energy range that is set for the direct incident gamma-rays.

The gamma radiation field acquisition part 31 of the image acquisition part 26 acquires a three-dimensional gamma radiation field of the direct incident gamma-rays from the incident gamma-ray information on the direct incident gamma-rays (step S31). Since the direct incident gamma-rays are those that enter the detectors 10 among direct gamma rays, the gamma radiation field acquired in step S31 is hereinafter referred to as a "direct gamma radiation field."

Note that the incident gamma-ray information used in step S31 and step S32 described later includes the scattering positions of the incident gamma-rays, in addition to the directions and energies thereof. That is, the gamma-ray image acquisition device 1 measures directions that include scattering positions. In this way, the gamma radiation field acquisition part 31 acquires the positions of the tracks of the incident gamma-rays relative to the chamber 11. Then, the tracks of a large number of incident gamma-rays are referenced to acquire a gamma radiation field by an analytic or statistical method. The direct gamma radiation field is acquired as a three-dimensional image and thus hereinafter referred to as a "direct gamma-ray image."

The gamma radiation field acquisition part 31 further acquires a three-dimensional scattered gamma radiation field of the scattered incident gamma-rays from the incident gamma-ray information on the scattered incident gamma-rays (step S32). A three-dimensional image that indicates the scattered gamma radiation field is hereinafter referred to as a "scattered gamma-ray image." Note that it is in principle possible to produce a three-dimensional gamma-ray image for each energy and to obtain an energy distribution of emitted gamma-rays for each position in the body. In other words, a board sense of imaging spectroscopy extended to three-dimensional images is made possible.

Accordingly, even direct gamma-rays that are emitted from a plurality of types of radioactive materials and have different energies can be measured simultaneously. In this case, the acquisition of a moving image by wide-field observation is also made possible for all radioactive materials. For example, in Boron Neutron Capture Therapy (BNCT), 511-keV gamma-rays and 478-keV boron gamma-rays, emitted from a tumor marked with a PET drug, can be separated from each other under a neutron beam to produce images thereof. In this case, the therapy can be done while the degree of biodistribution concentration of a boron product in the tumor is compared with the distribution of the PET drug.

More generally, the image acquisition part 26 identifies first incident gamma-rays falling within a first energy range and second incident gamma-rays falling within a second energy range different from the first energy range from among a plurality of incident gamma-rays. The image acquisition part 26 then acquires a first gamma-ray image that indicates a three-dimensional gamma radiation field from information on the first incident gamma-rays, and acquires a second gamma-ray image that indicates a three-dimensional gamma radiation field from information on the second incident gamma-rays. The first and second energy ranges preferably do not overlap each other, but depending on the application, they may partly overlap each other, or one of them may include the other. Accordingly, an image that indicates more useful information than conventional images can be acquired from the information obtained by the gamma-ray image acquisition device 1.

Besides, the method of image processing can be simplified because the same principle as that used in optical image capture is applied, and high accurate processing is made possible. The gamma-ray image acquisition device 1 has a wide field of view and thus can acquire a wide-range, high-precision gamma-ray image, even with use of only two detectors 10.

In the gamma-ray image acquisition device 1, information on the electron density distribution in the body, acquired in advance, is stored in the storage 33 for preparation. The electron density distribution is acquired by, for example, a method of obtaining and converting the amount of absorption of X-rays from an X-ray CT image into Compton scattering, or by measuring the transmission coefficient of a human body, using a radiation source provided outside the device.

The amount of gamma-rays scattered in the body is proportional to the gamma-ray intensity and the electron density. Since direct gamma-rays enter each position of the body from surroundings, the intensity of direct gamma-rays, i.e., the amount of direct gamma-rays coming from all directions, at a position x is an average value in a region of a certain size including the position x. Therefore, $f_{comp}=f_{av} \cdot n_e$ holds true, where $f_{comp}$ is the intensity of scattered gamma-rays (or a value corresponding to that intensity) at a given position x, $n_e$ is an electron density at the given position x, and $f_{av}$ is the average intensity of direct gamma-rays (or a value corresponding to that average intensity) in the vicinity of the position x.

On the other hand, the influence of direct gamma-rays coming from surroundings can be reduced by dividing $f_{RI}$ by $f_{av}$, where $f_{RI}$ is the intensity of direct gamma-rays (or a value corresponding to that intensity) at the position x in the direct gamma-ray image acquired in step S31. That is, a change in the degree of radioactive material concentration can be acquired distinctly by using $f_{RI}/f_{av}$, as the degree of radioactive material concentration, e.g., as a value corresponding to a standardized uptake value (SUV) in PET. Through the aforementioned processing, the corrector 32 corrects the direct gamma-ray image, using the scattered gamma-ray image and the electron density distribution (step S33). The correction method may be modified in various ways. Instead of the division, a subtraction may be performed. This correction produces quantitative distribution information on radioactive materials in the body. The display 27 displays a corrected direct gamma-ray image in three dimensions or in an arbitrary section (step S34). Note that images obtained by PET or SPECT correspond to the aforementioned $f_{RI}$.

Figure 12A:
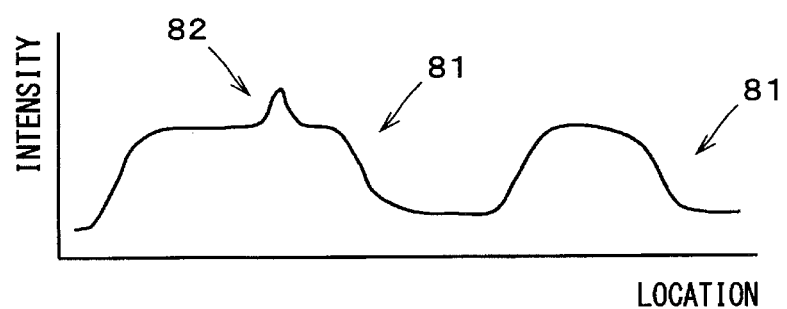
FIG. 12A is a diagram for describing how a direct gamma-ray image is corrected.
Figure 12B:
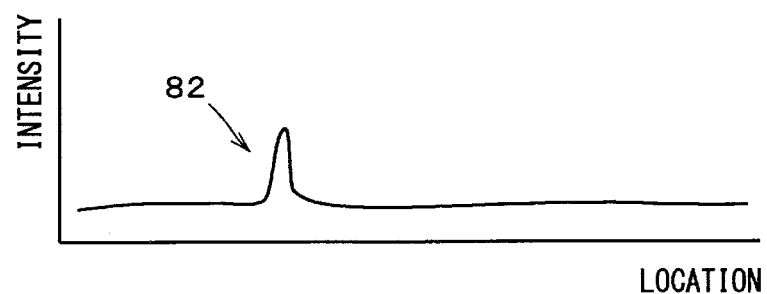
FIG. 12B is a diagram for describing how the direct gamma-ray image is corrected.

FIGS. 12A and 12B are diagrams for describing how the direct gamma-ray image is corrected. FIG. 12A schematically illustrates a change in intensity in the direct gamma-ray image. A region indicated by reference numeral 81 is where the intensity is high due to the presence of an organ with a large blood volume. A peak indicated by reference numeral 82 indicates the location of a tumor. FIG. 12B illustrates the direct gamma-ray image after correction. The influence of a change in electron density is reduced, and the location of the tumor appears relatively distinctly. Thus, it is possible to clearly confirm a region, such as a tumor in an organ, that has conventionally been unclear due to the brightness of surroundings. The above-described correction that makes clear the abnormal concentration of a radioactive material is particularly effective for such as brains, hearts, livers, and kidneys.

Incidentally, in PET, it is assumed that the direction connecting two hit pixels is the direction of a gamma-ray, according to the principle that two gamma-rays generated by positron-electron pair annihilation are measured at the same time in a large number of pixel elements surrounding the object. In PET, the actual directions of gamma-rays are not measured. Thus, gamma-rays arrive at each pixel from all forward directions within a solid angle of around 2π, and a large number of incidental events occur due to random noise or noise generated by scattered gamma-rays. As a result, noise against proper events increases. Even if PET employs a collimator, it does not provide a fundamental solution to the above-described problem because many scattered components are scattered within the collimator.

In contrast, the gamma-ray image acquisition device 1 can distinguish between gamma-rays emitted from a cone with a vertex angle corresponding to the full width at half maximum of the PSF and the other gamma-rays. That is, it is possible to distinguish only those events that are caused by gamma-rays within a cone of several degrees that extends toward an object, and to favorably separate the direct gamma-rays that are emitted from a radiation source within that range and the scattered gamma-rays in the body from the other gamma-rays. In addition, the direct gamma-rays and the scattered gamma-rays can be discriminated almost completely from each other by reference to energy information. As a result, it is possible to image only the direct gamma-rays and to acquire a high-quality image with extremely low noise. In PET or SPECT, the directions of scattered gamma-rays outside a prescribed energy range cannot be obtained properly. In contrast, the gamma-ray image acquisition device 1 can properly measure even the directions of scattered gamma-rays and can determine the origins of the scattered gamma-rays. The gamma-ray image acquisition device 1 does not require the detectors to perform scans as in the case of PET, and the size of the device can be relatively small.

In the gamma-ray image acquisition device 1, unlike in PET, imaging is not affected by the distribution of sources of scattering or artifacts derived from a noise removal method. In PET, even if the dosage of a drug is increased in order to increase the occurrence of true events, the occurrence of incidental events increases with the square of the dosage, whereas the occurrence of true events is proportional to the amount of the drug. Thus, few effects are expected from increasing the amount of the drug. Compared to PET, the gamma-ray image acquisition device 1 achieves a considerable reduction in the dosage of a drug that is administered to a patient.

The gamma-ray image acquisition device 1 also achieves a considerable reduction in random noise and noise generated by unnecessary scattered gamma-rays, by restricting the energy range of incident gamma-rays, restricting the target scattered gamma-rays and the recoil electrons that are detected by the detectors 10, and restricting the incident directions of gamma-rays. Accordingly, compared to conventional Compton cameras and PET, the gamma-ray image acquisition device 1 can acquire an image with a considerable reduction in nose.

Figure 13:
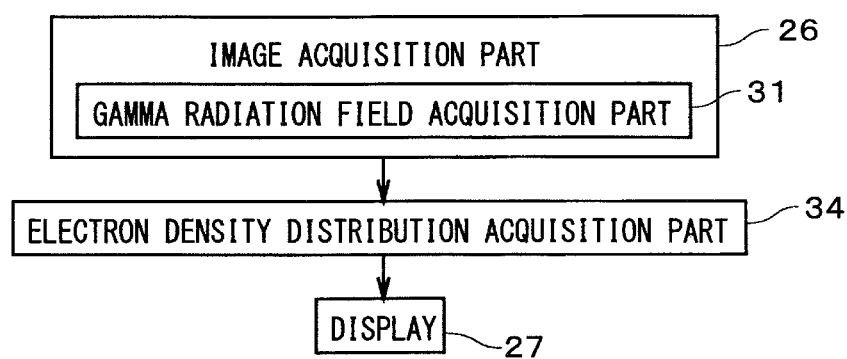
FIG. 13 illustrates some constituent elements of the gamma-ray image acquisition device.

By using the aforementioned principle, the gamma-ray image acquisition device 1 can also acquire the electron density distribution of an object. In this case, an electron density distribution acquisition part 34 is provided between the image acquisition part 26 and the display 27 as illustrated in FIG. 13.

Figure 14:
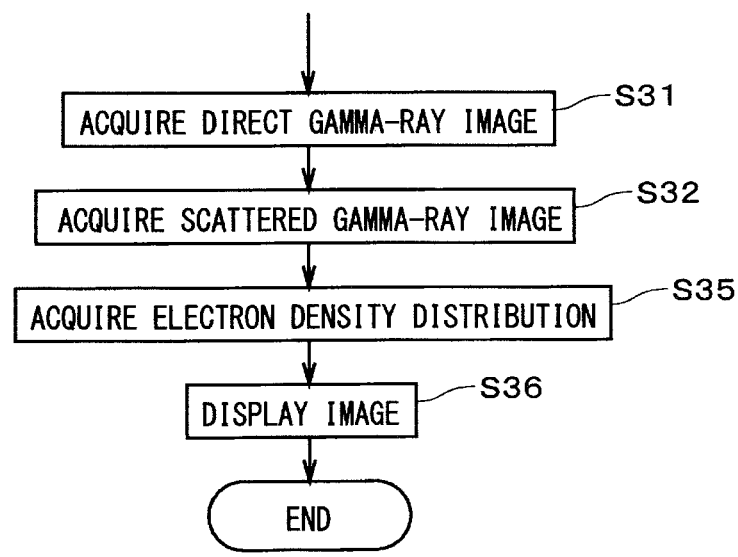
FIG. 14 illustrates some operations of the gamma-ray image acquisition device.

As illustrated in FIG. 14, after the three-dimensional direct gamma-ray image and the three-dimensional scattered gamma-ray image have been acquired in the same manner as in FIG. 11 (steps S31 and S32), the electron density distribution acquisition part 34 smooths the direct gamma-ray image so that the image is averaged by a region that extends to approximately a scattering length (e.g., 5 to 10 cm) of the direct gamma-rays. This smoothed image is regarded as $f_{av}$, and the electron density $n_e$ is acquired by obtaining $f_{comp}/f_{av}$. The electron density distribution acquisition part 34 performs this processing at each position so as to acquire the electron density distribution in the body, i.e., in the object, from the smoothed direct gamma-ray image and the scattered gamma-ray image (step S35). Since the intensity of scattered gamma-rays is proportional to the electron density within the aforementioned cone defined by the PSF, it is possible to image the electron density distribution in the body. The display 27 displays an image that indicates the electron density distribution in three dimensions or in an arbitrary section (step S36).

Since the gamma-ray image acquisition device 1 acquires the electron density distribution, it is possible to correct the amount of gamma-rays that are lost by being scattered in the body. The amount of scattering of gamma-rays depends on the distribution of substances in the body, and thus individual measurement becomes necessary. However, the gamma-ray image acquisition device 1 can simultaneously acquire the electron density distribution and the gamma-ray image.

In the case of obtaining the electron density distribution from X-ray CT, it is necessary to measure and convert photoelectric absorption coefficients in the body into electron densities. This requires additional correction because the photoelectric absorption is proportional to the fifth power of the atomic weight and is thus strongly affected by bones or other parts that contain heavy atoms. The gamma-ray image acquisition device 1 can acquire the electron density distribution through simple processing.

The electron density distribution can be used, for example, to correct the scattering of gamma-rays with respect to a SPECT drug, which has conventionally been difficult to correct, and thus can improve quantitative properties. In gamma-ray therapy, unlike in X-ray therapy, MeV-range photons are applied, and energy is given to the body by Compton scattering. Therapeutic effects in that body can be estimated by using the above-described electron density distribution in order to obtain a scattering coefficient at each location in the body.

Figure 15:
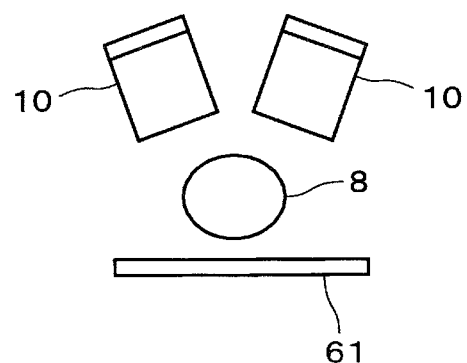
FIG. 15 illustrates the arrangement of detectors relative to a patient.

The next description is on another example of using the gamma-ray image acquisition device 1 for medical purposes. FIG. 15 illustrates the arrangement of detectors 10, viewed from the head side of a patient 8 who is lying on his or her back to be examined. A drug that contains a radioactive material that emits positrons is administered to the patient 8. The configuration of each detector 10 is the same as that described above. In the example in FIG. 15, two detectors 10 are arranged side by side in the right-left direction above the head of the patient 8. As in the case in FIG. 9, the gamma-ray image acquisition device 1 may be provided with the mover 51 that moves the two detectors 10 in parallel with the axis of the trunk of the patient 8, and the attachment parts 512 for installing additional detectors 10.

The gamma-ray image acquisition device 1 further includes a counter detector 61. The counter detector 61 has a plate-like shape and is disposed so as to sandwich the patient 8 between the detectors 10 and itself. In other words, the counter detector 61 is disposed on the side opposite to the chambers of the detectors 10, with the patient 8, i.e., an object, therebetween. The counter detector 61 acquires the detected positions and detected times, i.e., incident positions and incident times, of gamma-rays that enter from the object. The counter detector 61 is a "Timing Position Detector." The counter detector 61 detects the incident positions of gamma-rays with an accuracy of several millimeters (mm) and detects the incident times of the gamma-rays with an accuracy of sub-nanoseconds. The counter detector 61 also has high detection efficiency.

The incident directions of gamma-rays detected by the detectors 10 range widely. Thus, a difference in orientation between the two detectors 10 is preferably in the range of 0 to 60 degrees when one counter detector 61 is provided. However, when consideration is given to the case where a plurality of counter detectors 61 is provided as will be described later, the angle formed by the direction from the chamber 11 of one detector 10 (see FIG. 1) to the patient 8, i.e., object, and the direction from the chamber 11 of the other detector 10 to the object is preferably greater than or equal to 0 degrees and less than or equal to 140 degrees. Some of paired gamma-rays generated by electron-positron pair annihilation enter the chambers 11 of the detectors 10 as incident gamma-rays. The other some of the paired gamma-rays are incident on the counter detector 61.

Figure 16:
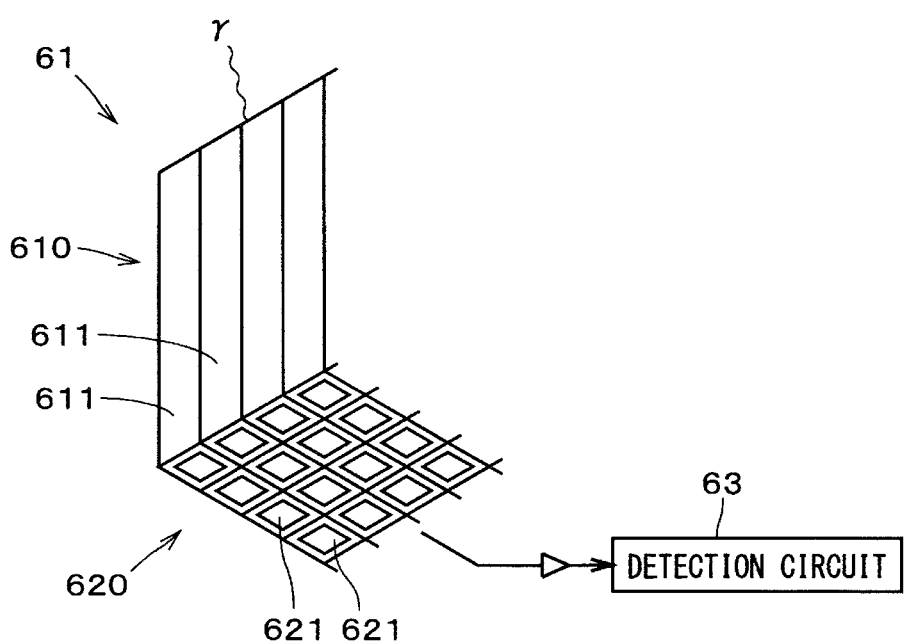
FIG. 16 illustrates the structure of a counter detector.

FIG. 16 is a perspective view illustrating a configuration of the counter detector 61. The counter detector 61 includes a two-dimensional scintillator array 610, a photodetector array 620, and a detection circuit 63. In the scintillator array 610, scintillators 611 are arranged two-dimensionally. Each scintillator 611 has a rod-like shape and is directed normal to the plane of arrangement. The scintillators 611 are preferably lead-containing plastic scintillators or lead-containing glass scintillators. These scintillators are low in price and thus help reducing the manufacturing cost of the gamma-ray image acquisition device 1.

The upper faces of the two-dimensionally arranged scintillators 611 constitute a plane of incidence that faces the patient 8 and the detectors 10. The "upper faces" as used herein are merely expressions for the purpose of explanation and not limited to the upper side in the gravitational direction. The scintillator array 610 functions as a pixel array when detecting gamma-rays. The dimension of one pixel is, for example, 2 mm square. The scintillators 611 have a length of several centimeters (cm).

The photodetector array 620 is disposed on the lower face of the scintillator array 610. The photodetector array 620 includes two-dimensionally arranged photodetectors 621.

Each photodetector 621 is disposed at the lower end of one scintillator 611. When gamma-rays emitted from the patient 8 are incident on the scintillators 611, the corresponding photodetectors 621 detect the light coming from the scintillators 611. As the photodetectors 621, high-speed and high-sensitivity photodetectors are used. The photodetectors 621 are, for example, avalanche photodetectors such as SiPM (Silicon Photomultipliers).

Signals from the photodetector array 620 are input to the detection circuit 63. On the basis of the signals, the detection circuit 63 records the detected positions and detected times of gamma-rays acquired by the counter detector 61. As the detection circuit 63, an FPGA (Field-Programmable Gate Array) is used.

The counter detector 61 acquires only the detected positions and detected times of gamma-rays and does not acquire the energies of the gamma-rays. Thus, the counter detector 61 can be manufactured at low cost.

Figure 17:
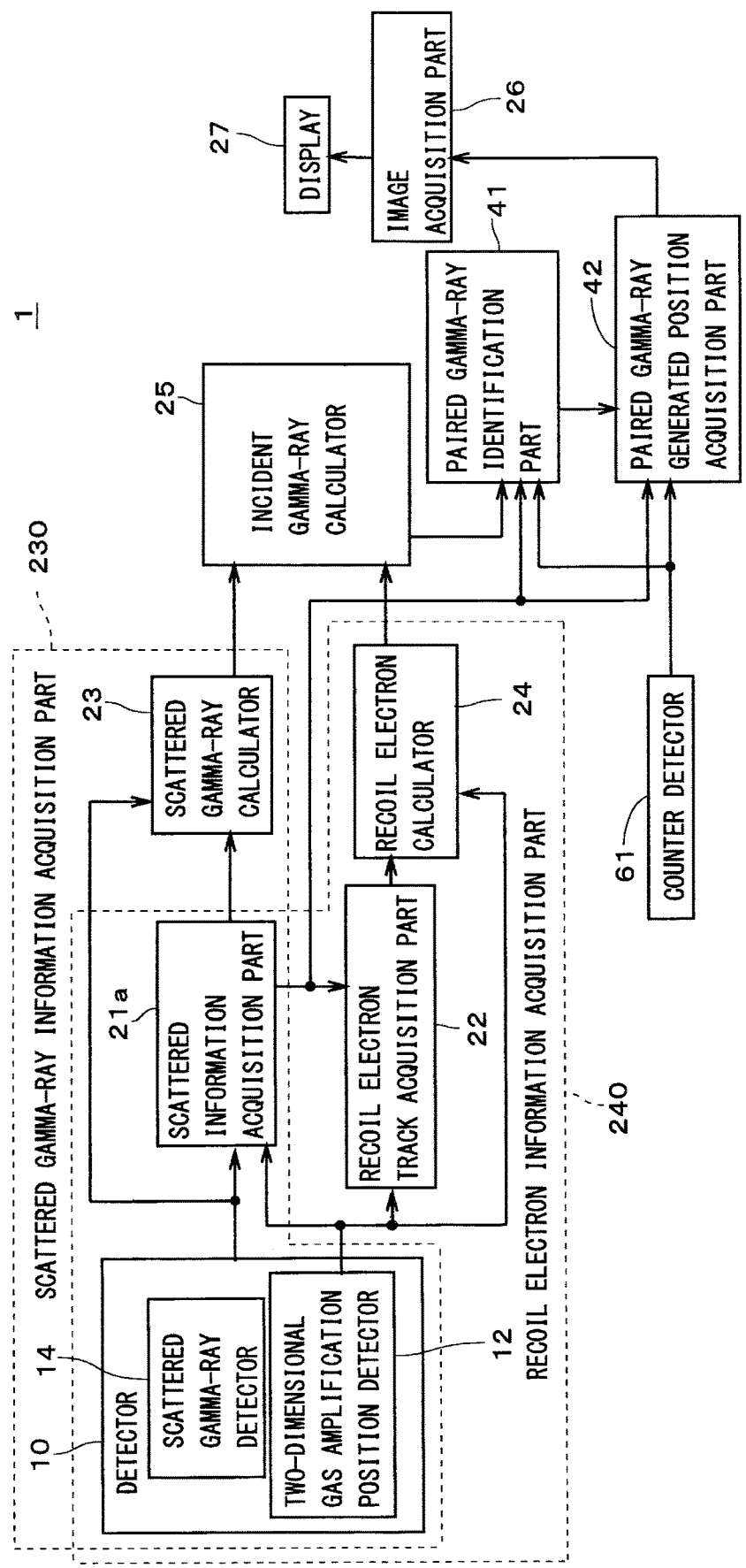
FIG. 17 is a block diagram illustrating a configuration of a gamma-ray image acquisition device.

FIG. 17 is a block diagram illustrating a configuration of the gamma-ray image acquisition device 1. The gamma-ray image acquisition device 1 differs from that in FIG. 2 in that the scattering position acquisition part 21 is replaced by a scattering information acquisition part 21a. The scattering information acquisition part 21a acquires the scattering time of an incident gamma-ray, in addition to the scattering position thereof. The scattering time is obtained from the time when the scattered gamma-ray enters the scattered gamma-ray detector 14, and the scattering position thereof.

In the gamma-ray image acquisition device 1 in FIG. 17, a paired gamma-ray identification part 41 and a paired gamma-ray generated position acquisition part 42 are provided between the incident gamma-ray calculator 25 and the image acquisition part 26. The paired gamma-ray identification part 41 receives input of the scattering position and scattering time from the scattering information acquisition part 21a, the incident direction and energy of an incident gamma-ray from the incident gamma-ray calculator 25, and the detected position and detected time of a gamma-ray from the counter detector 61. The paired gamma-ray generated position acquisition part 42 receives input of the scattering position and scattering time from the scattering information acquisition part 21a, and the detected position and detected time of a gamma-ray from the counter detector 61.

Figure 18:
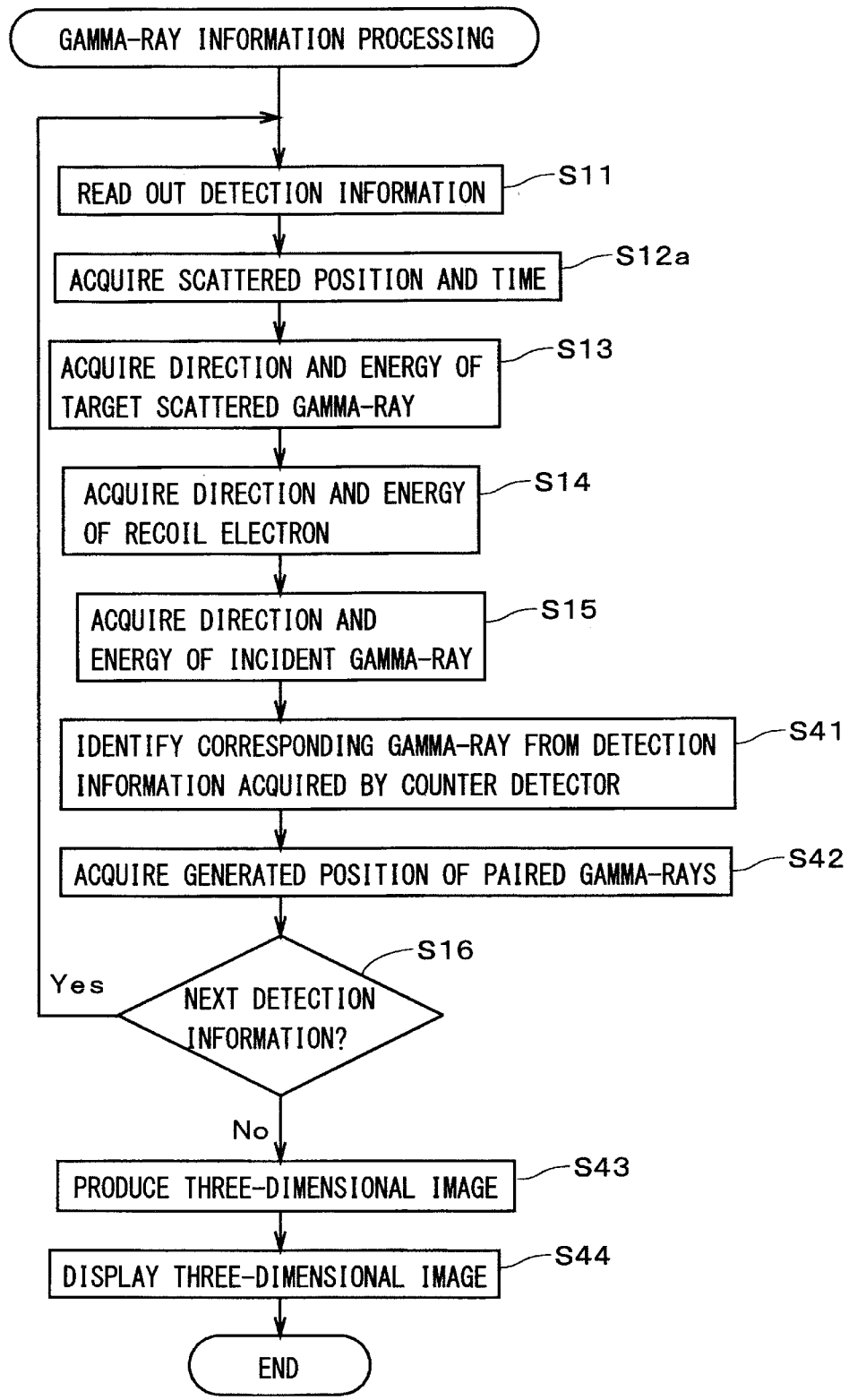
FIG. 18 illustrates a procedure of operations of the gamma-ray image acquisition device.

FIG. 18 illustrates a procedure of operations of the gamma-ray image acquisition device 1. Steps that are the same as those in FIG. 3 are given the same reference numerals. The procedure is based on the assumption that, prior to the operations illustrated in FIG. 18, there is a step of causing an incident gamma-ray to enter the chamber 11 from an external space to acquire detection information thereon (hereinafter, referred to as "first detection information"). There is also a step of causing the counter detector 61 to acquire the detected position and detected time of a gamma-ray entering from the patient 8 as second detection information.

In FIG. 18, the first detection information on one incident gamma-ray is read out in step S11. In the following description, the first detection information that corresponds to one gamma-ray is referred to as a "piece of first detection information" (the same applies to the second detection information). In step S12a, the scattering information acquisition part 21a acquires the scattering time, in addition to the scattering position in the chamber 11. Through steps S13 to S15, the direction and energy of the incident gamma-ray are acquired in the same manner as in FIG. 3.

Although not shown, in cases such as where the incident gamma-ray is not directed to the patient 8 and where the energy of the incident gamma-ray is not at 511 keV that is derived from electron-positron pair annihilation, the incident gamma-ray is regarded as not the gamma-ray that has directly entered from the patient 8, and is thus excluded from targets for subsequent arithmetic operations. The procedure then returns to step S11 via step S16 and transitions to processing for the next piece of first detection information.

In step S41 after step S15, considering the fact that paired gamma-rays generated by electron-positron pair annihilation propagate in opposite directions, the paired gamma-ray identification part 41 identifies a piece of second detection information that corresponds to the incident gamma-ray currently being processed from among the second detection information acquired by the counter detector 61. In other words, a piece of second detection information on the gamma-ray generated in a pair with the incident gamma-ray that has entered the detector 10 is identified from among a large number of pieces of second detection information that indicate a large number of combinations of the detected positions and detected times of gamma-rays, acquired by the counter detector 61. In this way, the paired gamma-rays, one entering the detector 10 and the other entering the counter detector 61, are identified.

Specifically, first a spatial range within which the other of the paired gamma-rays can be incident on the counter detector 61 is identified by the scattering position and incident direction of the incident gamma-ray in the detector 10, and pieces of second detection information on gamma-rays that have entered that range are selected. As described previously, the full width at half maximum of the point spread function that indicates the accuracy of the incident direction corresponds to a visual angle less than or equal to 15 degrees. The visual angle corresponding to the full width at half maximum is preferably less than or equal to 10 degrees, more preferably less than or equal to 7 degrees, and yet more preferably less than or equal to 3 degrees. Thus, the number of pieces of second detection information to be focused on is considerably narrowed down on the basis of the detection position included in each piece of second detection information.

Moreover, a range of times within which the other of the paired gamma-rays can be incident on the counter detector 61 is obtained from the scattering time of the incident gamma-ray. On the basis of the detected time acquired by the counter detector 61, either the second detection information on one gamma-ray is identified, or it turns out that there is no second detection information to be targeted for arithmetic operations. That is, when the other of the paired gamma-rays has been incident on the counter detector 61 without being scattered, one set of the detected position and the detected time is identified as the second detection information on that gamma-ray. In this way, although the counter detector 61 does not acquire the energy of the incident gamma-ray, an objective direct incident gamma-ray can be identified using the information received from the counter detector 61. The order in which consideration is given to the spatial restriction and the temporal restriction when identifying the second detection information may be reversed.

As described above, the paired gamma-ray identification part 41 identifies, from among the gamma-rays detected by the counter detector 61, a gamma-ray that has the detected position and detected time of a gamma-ray generated in a pair with the incident gamma-ray, on the basis of the incident direction, energy, scattering position, and scattering time of the incident gamma-ray that enters the chamber 11 of the detector 10. The details of the above-described arithmetic processing may be appropriately changed.

Although a plurality of detectors 10 is provided in FIG. 15, the counter detector 61 has a high spatial resolution and a high time resolution. Thus, it is possible to identify one piece of second detection information that is acquired from the counter detector 61 and that corresponds to one piece of first detection information acquired from each detector 10.

The generated position of the paired gamma-rays exists on a straight line that connects the scattering position acquired by the detector 10 and the detected position acquired by the counter detector 61. Based on this, in step S42, a three-dimensional position at which the paired gamma-rays have been generated is obtained with precision from the scattering position of one of the paired gamma-rays, the detected position of the other of the paired gamma-rays acquired by the counter detector 61, and a difference between the time when one of the paired gamma-rays has reached the scattering position and the time when the other of the paired gamma-rays has been detected by the counter detector 61.

By repeating steps S11 to S15, S41, and S42 for all pieces of first detection information, the image acquisition part 26 acquires a large number of generated positions of paired gamma-rays, i.e., the distribution of presence of the drug administered to the patient 8, as a three-dimensional image (step S43). The three-dimensional image is displayed on the display 27 (step S44). The order of the above-described processing may be appropriately changed in an available range.

While the above description mainly directs attention to one of the detectors 10, the same processing is also performed in the other detector 10. That is, the gamma-ray image acquisition device 1 also has the same configuration for the chamber 11 of the other detector 10, in which the generated position of paired gamma-rays is acquired from information on the scattering of the incident gamma-ray that enters the chamber 11 and information on gamma-rays that are incident on the counter detector 61. Note that the configuration regarding arithmetic operations may be shared between the two detectors 10, or may be provided separately for the two detectors 10.

In TOF (Time-of-Flight)-PET that has already been put to practical use, a large number of detectors having the same structure are disposed around a patient to estimate gamma-rays that are generated in a pair from the detected times of the gamma-rays and obtain the generated position of that pair of gamma-rays. Compared to conventional PET, TOF-PET improves the contrast of images. However, both in TOF-PET and conventional PET, noises such as scattered gamma-rays and incidental events occur in the same manner. To identify the gamma-rays generated in a pair, a detection time interval of approximately 4 ns is necessary when considering the size of a human body, and incidental events can occur within that time range. Also, the probability of at least one of the paired gamma-rays being scattered in a human body is approximately 50%, so that noise equivalent to or more than signals can occur.

In contrast, the gamma-ray image acquisition device 1 can acquire only information on gamma-rays that have a specific energy while using the TOF technique. As a result, it is possible to handle only information on paired gamma-rays that are not scattered. Also, only proper paired gamma-rays can be acquired because incidental occurrence of events in one detector 10 can be eliminated using the directions of incident gamma-rays that enter the other detector 10. Besides, an increase in the cost of the gamma-ray image acquisition device 1 can be suppressed because position detection and time detection are implemented by the counter detector 61 that is low in cost but has a position resolution of several millimeters (mm) and a time resolution of sub-nanoseconds. In the gamma-ray image acquisition device 1, the detectors 10 and the counter detector 61 that have different structures detect paired gamma-rays while dividing roles.

By using the counter detector 61 having a high spatial resolution and a high time resolution in a plane, two of the three dimensions of the generated position of paired gamma-rays can be acquired with, for example, an extremely high degree of accuracy of approximately 1 mm in a body about the size of a human body. This shows a 10-times improvement in angular resolution in the direction of gamma-rays that enter the detector 10, over the case where the counter detector 61 is not used. The remaining one-dimension, i.e., the direction of propagation of gamma-rays, can be acquired with, for example, accuracy of approximately 1 to 2 cm in the body, using the TOF technique.

With the combination of the detectors 10 and the counter detector 61, it is possible to effectively impose the spatial and temporal restrictions for coincidence counting of paired gamma-rays, to considerably reduce incidental and scattering noise, and to acquire pure signals. As a result, a low-dose, high-precision three-dimensional gamma-ray image can be acquired. This gamma-ray image is a three-dimensional image of an RI distribution in the body, acquired on the basis of gamma-ray measurement. Even if a dosage of a necessary drug is reduced to one-tenth or less of that in PET, an equivalent image can be obtained and no artifacts appear because of little noise. A dosage of a drug can be further reduced by increasing the number of detectors 10.

In the gamma-ray image acquisition device 1, there is little noise and each detector 10 operates independently. Thus, even if the number of detectors 10 is increased and the area of inspection is extended, incidental events will not increase, unlike in PET. Thus, even a whole body can be observed at a time. In PET, the distance between the detection points of paired gamma-rays needs to be set to approximately 80 cm because a large number of detectors are disposed around a human body. In contrast, in the gamma-ray image acquisition device 1, the detectors 10 and the counter detector 61 can be disposed in close proximity to a human body, and therefore it is possible to set the distance therebetween to approximately 40 cm. Accordingly, a wide range of human body can be measured with a small number of detectors 10.

Figure 19:
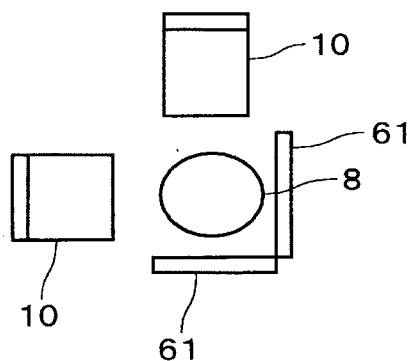
FIG. 19 illustrates the arrangement of detectors relative to a patient.

FIG. 19 illustrates another example of the arrangement of detectors 10 and counter detectors 61. In FIG. 19, the orientations of the two detectors 10 differ by 90 degrees. Each of the two detectors 10 and each of the two counter detectors 61 face each other. The patient 8 is positioned between each detector 10 and each opposing counter detector 61.

As described previously, the gamma-ray image acquisition device 1 has relatively low accuracy in measuring the generated position of paired gamma-rays in the direction of propagation of the gamma-rays. In view of this, the two detectors 10 are disposed in 90-degree different orientations to face the same part of the patient 8. This improves overall precision in the image of the generated position of the paired gamma rays. Note that the difference in orientation between the two detectors 10 may be approximately 90 degrees and preferably set in the range of 60 to 120 degrees.

Figure 20:
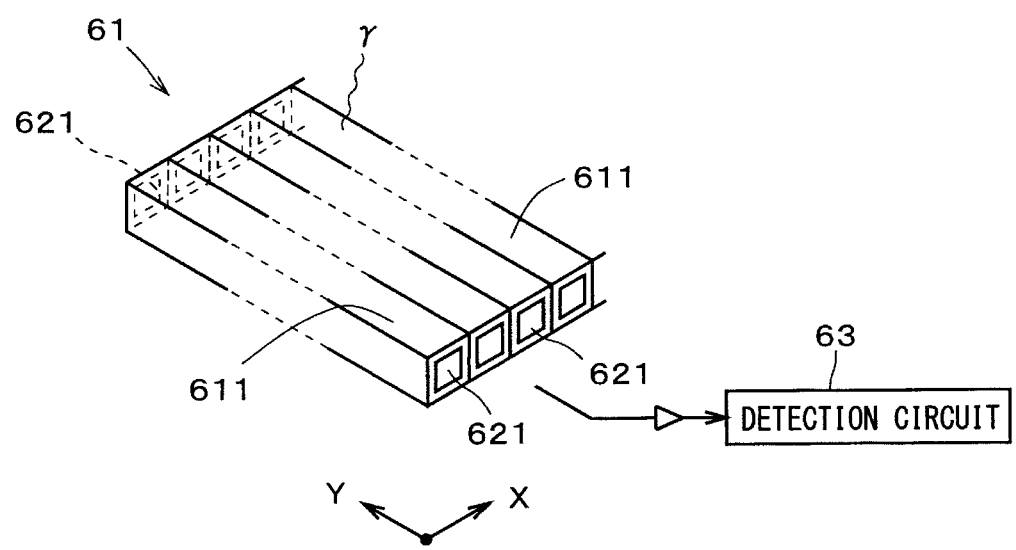
FIG. 20 illustrates another example of the counter detector.

FIG. 20 illustrates another example of the counter detector 61. In the counter detector 61 in FIG. 20, long rod-like scintillators 611 are arranged in a line so as to lie on a plane. The scintillators 611 are preferably lead-containing plastic scintillators or lead-containing glass scintillators. In FIG. 20, the direction of extension of each scintillator 611 is shown as a Y direction, and the direction of arrangement of the scintillators 611 as an X direction. The Y direction is perpendicular to the X direction. The plane of incidence of gamma-rays corresponds to the side faces of the scintillators 611. Each scintillator 611 has photodetectors 621 provided on the end faces. The detection circuit 63 obtains the Y-direction incident position and incident time of a gamma-ray incident on each scintillator 611 on the basis of times when the photodetectors 621 at the opposite ends detect light and a difference between the times. The detection circuit 63 performs only digital processing and does not use the magnitudes of signals.

The X-direction incident position corresponds to the position of the scintillator 611 on which the gamma-ray has been incident. Thus, a 1- to 2-mm resolution can be obtained. Accuracy in the Y-direction position is approximately 1 cm. However, compared to the case in FIG. 16, the number of readouts is reduced by an order or more of magnitude, and the cost can be reduced to one several times of that in the case in FIG. 16.

Figure 21:
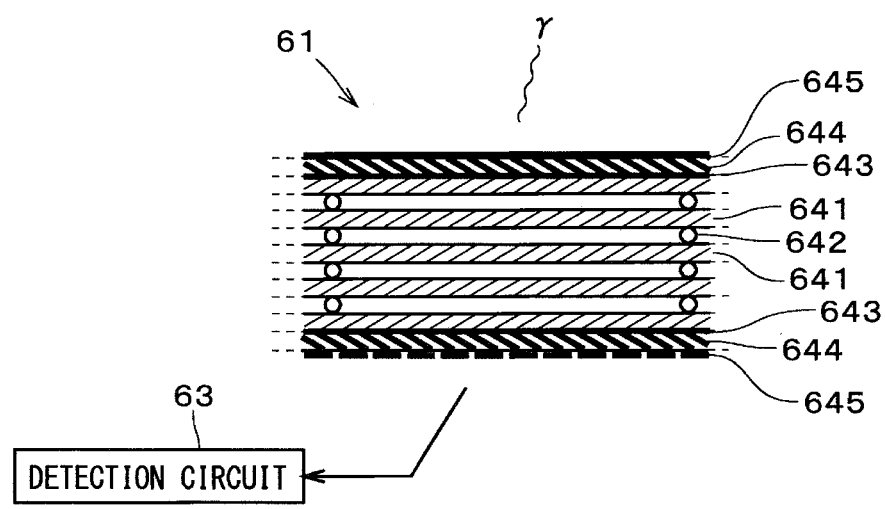
FIG. 21 illustrates yet another example of the counter detector.

FIG. 21 illustrate yet another example of the counter detector 61. The counter detector 61 in FIG. 21 uses the technique of Multi-Gap Resistive Plate Chambers. In the counter detector 61, glass plates 641 that are high-resistance plates and spacers 642 are alternately arranged, forming a multi-layer chamber. Electrodes 643 are provided respectively on the upper face of the uppermost glass plate 641 and on the lower face of the lowermost glass plate 641. A high potential difference is applied between these electrodes 643. On each outer side of the pair of electrodes, a readout electrode 645 is provided via an insulating layer 644. The readout electrodes 645 are in the form of stripes, and the direction in which each electrode line of the upper readout electrode 645 extends differs by 90 degrees from the direction in which each electrode line of the lower readout electrode 645 extends.

An inert gas is sealed in the multi-layer chamber, and a spark occurs when a gamma-ray that enters the glass plates 641 is converted into an electron in glass and the electron is emitted into the gas while an intense electric field is applied by the electrodes 643. Signals at this time are as high as several kilovolts (kV), so that induced signals are extracted from the upper and lower readout electrodes 645. The time resolution is several tens of picoseconds (ps), and the position resolution in two dimensions can also be less than or equal to 1 mm. With the configuration in FIG. 21, an extremely low-cost and large-area counter detector 61 can be achieved.

As the counter detector 61, any of various types of detectors can be employed as long as it has a high response speed. By providing the low-cost counter detector 61 that does not acquire the energies of gamma-rays, the generated positions of paired gamma-rays can be acquired at low cost and with high accuracy. The number of counter detectors 61 may be three or more. A configuration is also possible in which the number of detectors 10 is one, and a plurality of counter detectors 61 is provided. The shape of the counter detector 61 is not limited to a flat plate-like shape. For example, the counter detector 61 may have a curved shape. Also, the number of detectors 10 may be changed to various values according to the dimensions of a to-be-measured part.

The scintillators of the counter detector 61 may be other than lead-containing plastic scintillators and lead-containing glass scintillators.

The gamma-ray image acquisition device 1 may be modified in various ways.

For example, only one detector 10 may be used to acquire a gamma radiation field. Alternatively, three or more detectors 10 may be used to measure one region. The number of detectors 10 to be used in measuring one region is preferably two. As another alternative, one region may be measured while changing the position of one detector 10 in sequence to a plurality of positions.

An object that emits incident gamma-rays may be any of various objects other than a human body as long as it contains a radioactive material. For example, the object may be high-density such as metal or concrete that is not capable of normal X-ray non-destructive tests. In this case, the internal diagnosis of the object becomes possible. Also, degradation tests for piping or the like become possible. The object may also be an animal or a plant. The object is not limited to a human body also in the case where the object contains a substance that emits positrons.

The configurations of the scattered gamma-ray information acquisition part 230 and the recoil electron information acquisition part 240 may be modified in various ways. Also, different detection principles from those described above may be adopted for these configurations. The order of arithmetic processing may also be appropriately changed in an available range.

The configurations of the above-described preferred embodiments and variations may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST

1 Gamma-ray image acquisition device
8 Patient
11 Chamber
14 Scattered gamma-ray detector
21 Scattering position acquisition part
21a Scattering information acquisition part
25 Incident gamma-ray calculator
26 Image acquisition part
32 Corrector
33 Storage
34 Electron density distribution acquisition part
41 Paired gamma-ray identification part
42 Paired gamma-ray generated position acquisition part
61 Counter detector
91 Incident gamma-ray
92 Target scattered gamma-ray
93 Recoil electron
231 Scattering direction acquisition part
240 Recoil electron information acquisition part
512 Attachment part
611 Scintillator
S11 to S16, S12a, S21, S31 to S33, S35, S41 to S43 Step

The invention claimed is:

1. A gamma-ray image acquisition device using Compton scattering, comprising:
   a chamber;
   a scattered gamma-ray detector for detecting a target scattered gamma-ray generated by Compton scattering of an incident gamma-ray that enters said chamber from an external space, and acquiring a detected position and energy of said target scattered gamma-ray;
   a scattering position acquisition part for acquiring a scattering position of said incident gamma-ray in said chamber;
   a scattering direction acquisition part for acquiring a direction of said target scattered gamma-ray on the basis of said scattering position and said detected position;
   a recoil electron information acquisition part for acquiring a direction and energy of a recoil electron recoiling from said scattering position;
   an incident gamma-ray calculator for acquiring an incident direction and energy of the corresponding incident gamma-ray from the direction and energy of said target scattered gamma-ray and the direction and energy of said recoil electron; and
   an image acquisition part for acquiring a two-dimensional image by imaging spectroscopy based on incident directions and energies of a plurality of incident gamma-rays, the two-dimensional image being an image in which each pixel corresponding to the incident direction of incident gamma-rays includes energy distribution information,
   wherein in said two-dimensional image, an area and a solid angle of an imaging range are proportional to each other, energy distribution of said each pixel indicates quantitative radiation intensity per unit area at a spot corresponding to said each pixel, and
   a full width at half maximum of a point spread function that indicates accuracy of said incident direction acquired by said incident gamma-ray calculator corresponds to a visual angle less than or equal to 15 degrees.

2. The gamma-ray image acquisition device according to claim 1, wherein
   said image acquisition part identifies at least either ones of direct incident gamma-rays and scattered incident gamma-rays from among said plurality of incident gamma-rays and acquiring a distribution of the incident directions of said at least either gamma-rays as a two-dimensional image, the direct incident gamma-rays directly entering said chamber from a radiation source, and the scattered incident gamma-rays falling within an energy range lower than an energy range of said direct incident gamma-rays.

3. A gamma-ray image acquisition device using Compton scattering, comprising:
   a chamber;
   a scattered gamma-ray detector for detecting a target scattered gamma-ray generated by Compton scattering of an incident gamma-ray that enters said chamber from an object which is a human body to which a drug that emits positrons or gamma-rays is administered, and acquiring a detected position and energy of said target scattered gamma-ray;
   a scattering position acquisition part for acquiring a scattering position of said incident gamma-ray in said chamber;
   a scattering direction acquisition part for acquiring a direction of said target scattered gamma-ray on the basis of said scattering position and said detected position;

a recoil electron information acquisition part for acquiring a direction and energy of a recoil electron recoiling from said scattering position;

an incident gamma-ray calculator for acquiring an incident direction and energy of the corresponding incident gamma-ray from the direction and energy of said target scattered gamma-ray and the direction and energy of said recoil electron; and an image acquisition part for identifying first incident gamma-rays that directly enter said chamber from a radiation source and second incident gamma-rays falling within an energy range lower than an energy range of said direct incident gamma-rays from among a plurality of incident gamma-rays, acquiring a first gamma-ray image that indicates a three-dimensional gamma radiation field from information on said first incident gamma-rays, and acquiring a second gamma-ray image that indicates a three-dimensional gamma radiation field from information on said second incident gamma-rays;

a storage for storing an electron density distribution in said object, provided in advance; and a corrector for correcting said first gamma-ray image by using said second gamma-ray image and said electron density distribution to obtain quantitative distribution information of radioactive substance in said object, wherein a full width at half maximum of a point spread function that indicates accuracy of said incident direction acquired by said incident gamma-ray calculator corresponds to a visual angle less than or equal to 15 degrees.

4. A gamma-ray image acquisition device using Compton scattering, comprising:

a chamber;

a scattered gamma-ray detector for detecting a target scattered gamma-ray generated by Compton scattering of an incident gamma-ray that enters said chamber from an external space, and acquiring a detected position and energy of said target scattered gamma-ray;

a scattering position acquisition part for acquiring a scattering position of said incident gamma-ray in said chamber;

a scattering direction acquisition part for acquiring a direction of said target scattered gamma-ray on the basis of said scattering position and said detected position;

a recoil electron information acquisition part for acquiring a direction and energy of a recoil electron recoiling from said scattering position;

an incident gamma-ray calculator for acquiring an incident direction and energy of the corresponding incident gamma-ray from the direction and energy of said target scattered gamma-ray and the direction and energy of said recoil electron;

an image acquisition part for identifying first incident gamma-rays that directly enter said chamber from a radiation source and second incident gamma-rays falling within an energy range lower than an energy range of said direct incident gamma-rays from among a plurality of incident gamma-rays, acquiring a first gamma-ray image that indicates a three-dimensional gamma radiation field from information on said first incident gamma-rays, and acquiring a second gamma-ray image that indicates a three-dimensional gamma radiation field from information on said second incident gamma-rays; and an electron density distribution acquisition part for smoothing said first gamma-ray image and acquiring an electron density distribution in said object from said first gamma-ray image that has been smoothed and said second gamma-ray image;

wherein a full width at half maximum of a point spread function that indicates accuracy of said incident direction acquired by said incident gamma-ray calculator corresponds to a visual angle less than or equal to 15 degrees.

5. The gamma-ray image acquisition device according to claim 3, further comprising:

an attachment part for installing an additional chamber same as said chamber.

6. A gamma-ray image acquisition device using Compton scattering, comprising:

a chamber that some of paired gamma-rays generated by electron-positron pair annihilation occurring in an object enter, each as an incident gamma-ray, the object containing a substance that emits positrons;

a scattered gamma-ray detector for detecting a target scattered gamma-ray generated by Compton scattering of said incident gamma-ray in said chamber and acquiring a detected position and energy of said target scattered gamma-ray;

a scattering information acquisition part for acquiring a scattering position and scattering time of said incident gamma-ray in said chamber;

a scattering direction acquisition part for acquiring a direction of said target scattered gamma-ray on the basis of said scattering position and said detected position of said target scattered gamma-ray;

a recoil electron information acquisition part for acquiring a direction and energy of a recoil electron recoiling from said scattering position;

an incident gamma-ray calculator for acquiring an incident direction and energy of the corresponding incident gamma-ray from the direction and energy of said target scattered gamma-ray and the direction and energy of said recoil electron;

a counter detector disposed on a side opposite to said chamber with said object therebetween, and for acquiring a detected position and detected time of a gamma-ray that enters from said object, said counter detector not acquiring energy of said gamma-ray;

a paired gamma-ray identification part for identifying, from among the gamma-rays detected by said counter detector, a gamma-ray that has the detected position and detected time of a gamma-ray generated in a pair with an incident gamma-ray that enters said chamber, on the basis of the incident direction, energy, scattering position, and scattering time of said incident gamma-ray;

a paired gamma-ray generated position acquisition part for acquiring a generated position, in said object, of the paired gamma-rays identified by said paired gamma-ray identification part, on the basis of the scattering position and scattering time of one of said paired gamma-rays in said chamber and the detected position and detected time of the other of said paired gamma-rays detected by said counter detector; and an image acquisition part for acquiring generated positions of a plurality of paired gamma-rays as a three-dimensional image, wherein a full width at half maximum of a point spread direction that indicates accuracy of said incident direction acquired by said incident gamma-ray calculator corresponds to a visual angle less than or equal to 15 degrees.

7. The gamma-ray image acquisition device according to claim 6, wherein
said counter detector includes a lead-containing plastic scintillator or a lead-containing glass scintillator.

8. The gamma-ray image acquisition device according to claim 6, further comprising:
another chamber same as said chamber; and
a configuration of acquiring a generated position of paired gamma-rays from information on scattering of an incident gamma-ray that enters said another chamber and information on a gamma-ray that is incident on said counter detector, as in the case of said chamber,
wherein an angle formed by a direction from said chamber to said object and a direction from said another chamber to said object is greater than or equal to 0 degrees and less than or equal to 140 degrees.

9. A gamma-ray image acquisition method comprising:
a) causing an incident gamma-ray to enter a chamber from an external space;
b) acquiring a direction and energy of a target scattered gamma-ray generated by Compton scattering of said incident gamma-ray in said chamber;
c) acquiring a direction and energy of a recoil electron that corresponds to said target scattered gamma-ray;
d) acquiring an incident direction and energy of said incident gamma-ray from the direction and energy of said target scattered gamma-ray and the direction and energy of said recoil electron; and
e) acquiring a two-dimensional image by imaging spectroscopy based on incident directions and energies of a plurality of incident gamma-rays acquired in said operation d), the two-dimensional image being an image in which each pixel corresponding to the incident direction of each incident gamma-ray includes energy distribution information,
wherein in said two-dimensional image, an area and a solid angle of an imaging range are proportional to each other, energy distribution of said each pixel indicates quantitative radiation intensity per unit area at a spot corresponding to said each pixel, and
a full width at half maximum of a point spread function that indicates accuracy of said incident direction acquired in said operation d) corresponds to a visual angle less than or equal to 15 degrees.

10. A gamma-ray image acquisition method comprising:
a) causing an incident gamma-ray to enter a chamber from an object which is a human body to which a drug that emits positrons or gamma-rays is administered;
b) acquiring a direction and energy of a target scattered gamma-ray generated by Compton scattering of said incident gamma-ray in said chamber;
c) acquiring a direction and energy of a recoil electron that corresponds to said target scattered gamma-ray;
d) acquiring an incident direction and energy of said incident gamma-ray from the direction and energy of said target scattered gamma-ray and the direction and energy of said recoil electron;
e) identifying first incident gamma-rays that directly enter said chamber from a radiation source and second incident gamma-rays falling within an energy range lower than an energy range of said direct incident gamma-rays from among a plurality of incident gamma-rays acquired in said operation d), acquiring a first gamma-ray image that indicates a three-dimensional gamma radiation field from information on said first incident gamma-rays, and acquiring a second gamma-ray image that indicates a three-dimensional gamma radiation field from information on said second incident gamma-rays; and
f) correcting said first gamma-ray image by using said second gamma-ray image and an electron density distribution in said object to obtain quantitative distribution information of radioactive substance in said object,
wherein a full width at half maximum of a point spread function that indicates accuracy of said incident direction acquired in said operation d) corresponds to a visual angle less than or equal to 15 degrees.

11. A gamma-ray image acquisition method comprising:
a) causing some of paired gamma-rays generated by electron-positron pair annihilation occurring in an object to enter a chamber, each as an incident gamma-ray, the object containing a substance that emits positrons;
b) acquiring a scattering position and scattering time of said incident gamma-ray due to Compton scattering thereof in said chamber;
c) acquiring a direction and energy of a target scattered gamma-ray generated by said Compton scattering of said incident gamma-ray;
d) acquiring a direction and energy of a recoil electron that corresponds to said target scattered gamma-ray;
e) acquiring an incident direction and energy of the corresponding incident gamma-ray from the direction and energy of said target scattered gamma-ray and the direction and energy of said recoil electron;
f) causing a counter detector to acquire a detected position and detected time of a gamma-ray that enters from said object, the counter detector being disposed on a side opposite to said chamber with said object therebetween, said counter detector not acquiring energy of said gamma-ray;
g) identifying, from among the gamma-rays detected by said counter detector, a gamma-ray that has the detected position and detected time of a gamma-ray generated in a pair with an incident gamma-ray that enters said chamber, on the basis of the incident direction, energy, scattering position, and scattering time of said incident gamma-ray;
h) acquiring a generated position, in said object, of paired gamma-rays identified in said operation g), on the basis of the scattering position and scattering time of one of said paired gamma-rays in said chamber and the detected position and detected time of the other of said paired gamma-rays detected by said counter detector; and
i) repeating said operations g) and h) to acquire generated positions of a plurality of paired gamma-rays as a three-dimensional image,
wherein a full width at half maximum of a point spread function that indicates accuracy of said incident direction acquired by said incident gamma-ray calculator corresponds to a visual angle less than or equal to 15 degrees.

12. A gamma-ray image acquisition method comprising:
a) causing an incident gamma-ray to enter a chamber from an external space;
b) acquiring a direction and energy of a target scattered gamma-ray generated by Compton scattering of said incident gamma-ray in said chamber;
c) acquiring a direction and energy of a recoil electron that corresponds to said target scattered gamma-ray;

d) acquiring an incident direction and energy of said incident gamma-ray from the direction and energy of said target scattered gamma-ray and the direction and energy of said recoil electron;

e) identifying first incident gamma-rays that directly enter said chamber from a radiation source and second incident gamma-rays falling within an energy range lower than an energy range of said direct incident gamma-rays from among a plurality of incident gamma-rays acquired in said operation d), acquiring a first gamma-ray image that indicates a three-dimensional gamma radiation field from information on said first incident gamma-rays, and acquiring a second gamma-ray image that indicates a three-dimensional gamma radiation field from information on said second incident gamma-rays; and f) smoothing said first gamma-ray image and acquiring an electron density distribution in said object from said first gamma-ray image that has been smoothed and said second gamma-ray image, wherein a full width at half maximum of a point spread function that indicates accuracy of said incident direction acquired in said operation d) corresponds to a visual angle less than or equal to 15 degrees.

13. The gamma-ray image acquisition device according to claim 4, further comprising:

an attachment part for installing an additional chamber same as said chamber.

\* \* \* \* \*